US011951018B2

(12) United States Patent
Sack

(10) Patent No.: US 11,951,018 B2
(45) Date of Patent: Apr. 9, 2024

(54) IMPLANT WITH IMPROVED FLOW CHARACTERISTICS

(71) Applicant: Institute for Musculoskeletal Science and Education, Ltd., King of Prussia, PA (US)

(72) Inventor: James A. Sack, Wayne, PA (US)

(73) Assignee: Institute for Musculoskeletal Science and Education, Ltd., King of Prussia, PA (US)

(*) Notice: Subject to any disclaimer, the term of this patent is extended or adjusted under 35 U.S.C. 154(b) by 64 days.

(21) Appl. No.: 17/194,999

(22) Filed: Mar. 8, 2021

(65) Prior Publication Data

US 2021/0346171 A1 Nov. 11, 2021

Related U.S. Application Data

(63) Continuation of application No. 15/819,930, filed on Nov. 21, 2017, now Pat. No. 10,940,015.

(51) Int. Cl.
*A61F 2/44* (2006.01)
*A61F 2/28* (2006.01)
(Continued)

(52) U.S. Cl.
CPC .......... *A61F 2/4455* (2013.01); *A61F 2/2846* (2013.01); *A61F 2/30767* (2013.01);
(Continued)

(58) Field of Classification Search
CPC ....................... A61F 2/5046; A61F 2002/5049
See application file for complete search history.

(56) References Cited

U.S. PATENT DOCUMENTS 3,720,959 A 3/1973 Hahn
4,038,703 A 8/1977 Bokros
(Continued)

FOREIGN PATENT DOCUMENTS

CN 101708138 5/2010
CN 103932841 7/2014
(Continued)

OTHER PUBLICATIONS

International Search Report and Written Opinion dated Feb. 8, 2019 for International Application No. PCT/US2018/62292.
(Continued)

*Primary Examiner* — Anu Ramana
(74) *Attorney, Agent, or Firm* — Plumsea Law Group, LLC

(57) ABSTRACT

An intervertebral implant comprising a body formed as an open truss structure, the body having a generally annular shape with a superior surface, an inferior surface, and a perimeter surface extending around an outer periphery of the body. The body may have a central portion and a peripheral portion, the peripheral portion extending inward from the perimeter surface toward the central portion, the peripheral portion including a first set of trusses, and the central portion including a second set of trusses. The implant may further include a strut at least partially defining a boundary between the central portion and the peripheral portion, wherein the strut has an oblong cross-sectional shape oriented to facilitate flow of bone graft material in a substantially radial direction away from the central axis.

20 Claims, 21 Drawing Sheets

(51) Int. Cl.
*A61F 2/30* (2006.01)
*A61B 17/68* (2006.01)
*A61F 2/46* (2006.01)
*A61L 27/36* (2006.01)

(52) U.S. Cl.
CPC ..... *A61B 17/68* (2013.01); *A61F 2002/30062* (2013.01); *A61F 2002/30112* (2013.01); *A61F 2002/30125* (2013.01); *A61F 2002/30156* (2013.01); *A61F 2002/30224* (2013.01); *A61F 2002/3023* (2013.01); *A61F 2002/30289* (2013.01); *A61F 2002/30593* (2013.01); *A61F 2002/3093* (2013.01); *A61F 2002/30985* (2013.01); *A61F 2002/4495* (2013.01); *A61F 2002/4629* (2013.01); *A61F 2250/0026* (2013.01); *A61L 27/3608* (2013.01)

(56) References Cited

U.S. PATENT DOCUMENTS

| | | |
|---|---|---|
| 4,309,777 A | 1/1982 | Patil |
| 4,759,769 A | 7/1988 | Hedman |
| 4,851,008 A | 7/1989 | Johnson |
| 4,889,685 A | 12/1989 | Shimamune |
| 4,917,704 A | 4/1990 | Frey |
| 4,961,740 A | 10/1990 | Ray et al. |
| 5,055,104 A | 10/1991 | Ray |
| 5,198,308 A | 3/1993 | Shetty et al. |
| 5,263,953 A | 11/1993 | Bagby |
| 5,306,310 A | 4/1994 | Siebels |
| 5,397,359 A | 3/1995 | Mittelmeier |
| 5,423,817 A | 6/1995 | Lin |
| 5,458,638 A | 10/1995 | Kuslich et al. |
| 5,571,185 A | 11/1996 | Schug |
| 5,571,192 A | 11/1996 | Schonhoffer |
| 5,607,424 A | 3/1997 | Tropiano |
| 5,609,635 A | 3/1997 | Michelson |
| 5,609,636 A | 3/1997 | Kohrs |
| 5,658,337 A | 8/1997 | Kohrs et al. |
| 5,709,683 A | 1/1998 | Bagby |
| 5,716,416 A | 2/1998 | Lin |
| D403,069 S | 12/1998 | Drewry et al. |
| 5,885,299 A | 3/1999 | Winslow |
| 5,888,223 A | 3/1999 | Bray, Jr. |
| 5,897,556 A | 4/1999 | Drewry et al. |
| 5,954,504 A | 9/1999 | Misch et al. |
| 5,968,098 A | 10/1999 | Winslow |
| 5,973,222 A | 10/1999 | Devanathan et al. |
| 6,010,502 A | 1/2000 | Bagby |
| 6,039,762 A | 3/2000 | McKay |
| 6,090,143 A | 7/2000 | Meriwether et al. |
| 6,102,948 A | 8/2000 | Brosnahan, III |
| 6,126,689 A | 10/2000 | Brett |
| 6,149,651 A | 11/2000 | Drewry et al. |
| 6,156,037 A | 12/2000 | LeHuec et al. |
| 6,200,348 B1 | 3/2001 | Biedermann et al. |
| 6,206,924 B1 | 3/2001 | Timm |
| 6,210,412 B1 | 4/2001 | Michelson |
| 6,371,987 B1 | 4/2002 | Weiland et al. |
| 6,428,575 B2 | 8/2002 | Koo et al. |
| 6,436,141 B2 | 8/2002 | Castro et al. |
| 6,464,727 B1 | 10/2002 | Sharkey |
| 6,468,309 B1 | 10/2002 | Lieberman |
| 6,494,883 B1 | 12/2002 | Ferree |
| 6,500,205 B1 | 12/2002 | Michelson |
| 6,520,996 B1 | 2/2003 | Manasas et al. |
| 6,527,805 B2 | 3/2003 | Studer et al. |
| 6,530,956 B1 | 3/2003 | Mansmann |
| 6,537,320 B1 | 3/2003 | Michelson |
| 6,558,423 B1 | 5/2003 | Michelson |
| 6,569,201 B2 | 5/2003 | Moumene |
| 6,582,431 B1 | 6/2003 | Ray |
| 6,582,467 B1 | 6/2003 | Teitelbaum et al. |
| 6,585,770 B1 | 7/2003 | White et al. |
| 6,616,695 B1 | 9/2003 | Crozet et al. |
| 6,666,888 B1 | 12/2003 | Jackson |
| 6,709,458 B2 | 3/2004 | Michelson |
| 6,758,849 B1 | 7/2004 | Michelson |
| 6,808,537 B2 | 10/2004 | Michelson |
| 6,846,327 B2 | 1/2005 | Khandkar et al. |
| 6,849,093 B2 | 2/2005 | Michelson |
| 6,863,689 B2 | 3/2005 | Ralph et al. |
| 6,923,810 B1 | 8/2005 | Michelson |
| 6,962,606 B2 | 11/2005 | Michelson |
| 6,997,953 B2 | 2/2006 | Chung et al. |
| 7,135,043 B2 | 11/2006 | Nakahara et al. |
| 7,141,068 B2 | 11/2006 | Ross et al. |
| 7,153,325 B2 | 12/2006 | Kim et al. |
| 7,186,267 B2 | 3/2007 | Aston et al. |
| 7,241,313 B2 | 7/2007 | Unwin et al. |
| 7,261,739 B2 | 8/2007 | Ralph |
| 7,297,162 B2 | 11/2007 | Mujwid |
| 7,341,601 B2 | 3/2008 | Eisermann et al. |
| 7,410,501 B2 | 8/2008 | Michelson |
| 7,429,270 B2 | 9/2008 | Baumgartner et al. |
| 7,435,261 B1 | 10/2008 | Castro |
| 7,452,369 B2 | 11/2008 | Barry |
| 7,465,318 B2 | 12/2008 | Sennett |
| 7,485,134 B2 | 2/2009 | Simonson |
| 7,527,649 B1 | 5/2009 | Blain |
| 7,534,254 B1 | 5/2009 | Michelson |
| 7,537,603 B2 | 5/2009 | Huebner et al. |
| 7,537,616 B1 | 5/2009 | Branch et al. |
| 7,575,598 B2 | 8/2009 | Albert |
| 7,611,217 B2 | 11/2009 | Shamoun et al. |
| 7,621,952 B2 | 11/2009 | Truckai et al. |
| 7,621,953 B2 | 11/2009 | Braddock, Jr. et al. |
| 7,628,814 B2 | 12/2009 | Studer et al. |
| 7,645,475 B2 | 1/2010 | Prewett |
| 7,655,043 B2 | 2/2010 | Peterman et al. |
| 7,794,500 B2 | 9/2010 | Felix |
| 7,799,056 B2 | 9/2010 | Sankaran |
| 7,803,191 B2 | 9/2010 | Biedermann et al. |
| 7,815,665 B2 | 10/2010 | Jahng |
| 7,846,207 B2 | 12/2010 | Lechmann et al. |
| 7,875,075 B2 | 1/2011 | Schwab |
| 7,879,100 B2 | 2/2011 | Denoziere |
| 7,879,103 B2 | 2/2011 | Gertzman et al. |
| 7,935,149 B2 | 5/2011 | Michelson |
| 8,016,887 B1 | 9/2011 | Castro |
| 8,021,424 B2 | 9/2011 | Beger et al. |
| 8,021,426 B2 | 9/2011 | Segal et al. |
| 8,062,365 B2 | 11/2011 | Schwab |
| 8,092,536 B2 | 1/2012 | Ahrens et al. |
| 8,142,507 B2 | 3/2012 | McGuckin, Jr. |
| 8,152,849 B2 | 4/2012 | Biedermann et al. |
| 8,182,538 B2 | 5/2012 | O'Neil et al. |
| 8,226,718 B2 | 7/2012 | Castro |
| 8,241,363 B2 | 8/2012 | Sommerich et al. |
| 8,246,683 B2 | 8/2012 | Castro |
| 8,252,059 B2 | 8/2012 | Overes et al. |
| 8,298,286 B2 | 10/2012 | Trieu |
| 8,303,879 B2 | 11/2012 | Bertele et al. |
| 8,343,224 B2 | 1/2013 | Lynn |
| 8,361,149 B2 | 1/2013 | Castro |
| 8,366,777 B2 | 2/2013 | Matthis et al. |
| D681,204 S | 4/2013 | Farris et al. |
| 8,414,654 B1 | 4/2013 | Ganey |
| 8,414,820 B2 | 4/2013 | Bertele et al. |
| 8,430,930 B2 | 4/2013 | Hunt |
| D681,812 S | 5/2013 | Farris et al. |
| 8,435,300 B2 | 5/2013 | Messerli et al. |
| 8,454,700 B2 | 6/2013 | Lemoine et al. |
| 8,475,533 B1 | 7/2013 | Castro |
| 8,551,173 B2 | 10/2013 | Lechmann et al. |
| 8,556,978 B2 | 10/2013 | Schaller |
| 8,568,413 B2 | 10/2013 | Mazur et al. |
| 8,613,769 B2 | 12/2013 | Sears et al. |
| 8,623,090 B2 | 1/2014 | Butler |
| 8,673,006 B2 | 3/2014 | Castro |
| 8,700,198 B2 | 4/2014 | Conway et al. |
| 8,702,808 B2 | 4/2014 | Teoh et al. |
| 8,709,042 B2 | 4/2014 | Greenhalgh et al. |

(56) References Cited

U.S. PATENT DOCUMENTS

| | | |
|---|---|---|
| 8,728,160 B2 | 5/2014 | Globerman |
| 8,740,981 B2 | 6/2014 | Tornier et al. |
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,840,614 B2 | 9/2014 | Mikhail et al. |
| 8,864,831 B2 | 10/2014 | Lee et al. |
| 8,894,661 B2 | 11/2014 | McDevitt |
| 8,900,310 B2 | 12/2014 | Carlson |
| 8,900,312 B2 | 12/2014 | McLean et al. |
| 8,932,356 B2 | 1/2015 | Kraus |
| 8,940,050 B2 | 1/2015 | Laurence |
| 8,940,052 B2 | 1/2015 | Lechmann et al. |
| 8,951,300 B2 | 2/2015 | Parrish |
| 8,986,383 B2 | 3/2015 | Castro |
| 9,011,499 B1 | 4/2015 | Kiester |
| 9,039,766 B1 | 5/2015 | Fonte |
| 9,060,876 B1 | 6/2015 | To |
| 9,101,491 B2 | 8/2015 | Rodgers |
| D739,935 S | 9/2015 | Blain et al. |
| 9,138,301 B2 | 9/2015 | Kita et al. |
| 9,155,819 B2 | 10/2015 | Fonte et al. |
| 9,186,252 B2 | 11/2015 | Leibinger |
| 9,186,257 B2 | 11/2015 | Geisler et al. |
| 9,220,518 B2 | 12/2015 | Neal et al. |
| 9,237,958 B2 | 1/2016 | Duggal et al. |
| 9,247,970 B2 | 2/2016 | Teisen |
| 9,254,199 B2 | 2/2016 | Biedermann et al. |
| 9,271,765 B2 | 3/2016 | Blain |
| 9,271,771 B2 | 3/2016 | Mathieu et al. |
| 9,271,845 B2 | 3/2016 | Hunt et al. |
| 9,289,308 B2 | 3/2016 | Marino et al. |
| 9,289,312 B2 | 3/2016 | Davenport et al. |
| 9,295,552 B2 | 3/2016 | Lechmann et al. |
| 9,364,330 B2 | 6/2016 | Lindsey et al. |
| 9,402,733 B1 | 8/2016 | To et al. |
| 9,408,651 B2 | 8/2016 | Sennett et al. |
| 9,421,108 B2 | 8/2016 | Hunt |
| 9,427,328 B2 | 8/2016 | Drochner |
| 9,433,510 B2 | 9/2016 | Lechmann et al. |
| 9,433,511 B2 | 9/2016 | Bagga et al. |
| 9,439,779 B2 | 9/2016 | Zhang et al. |
| 9,439,948 B2 | 9/2016 | Lin et al. |
| 9,445,317 B2 | 9/2016 | Dudda et al. |
| 9,452,056 B2 | 9/2016 | Early et al. |
| 9,452,064 B2 | 9/2016 | Trautwein et al. |
| 9,456,901 B2 | 10/2016 | Jones et al. |
| 9,456,907 B1 | 10/2016 | Castro |
| 9,517,095 B2 | 12/2016 | Vaidya |
| 9,522,028 B2 | 12/2016 | Warren et al. |
| 9,526,548 B2 | 12/2016 | Asfora |
| 9,545,317 B2 | 1/2017 | Hunt |
| 9,549,823 B2 | 1/2017 | Hunt et al. |
| 9,554,914 B2 | 1/2017 | Taylor et al. |
| 9,561,117 B2 | 2/2017 | Lechmann et al. |
| 9,566,095 B2 | 2/2017 | Lorio |
| 9,566,100 B2 | 2/2017 | Asfora |
| 9,572,669 B2 | 2/2017 | Hunt et al. |
| 9,597,197 B2 | 3/2017 | Lechmann et al. |
| 9,603,613 B2 | 3/2017 | Schoenefeld et al. |
| 9,622,880 B2 | 4/2017 | Dunworth et al. |
| 9,629,727 B2 | 4/2017 | Baynham |
| 9,636,226 B2 | 5/2017 | Hunt |
| 9,649,200 B2 | 5/2017 | Wickham |
| 9,662,128 B2 | 5/2017 | Reiley |
| 9,662,157 B2 | 5/2017 | Schneider et al. |
| 9,662,158 B2 | 5/2017 | Reiley |
| 9,662,224 B2 | 5/2017 | Weiman et al. |
| 9,662,226 B2 | 5/2017 | Wickham |
| 9,668,781 B2 | 6/2017 | Stark |
| 9,675,394 B2 | 6/2017 | Reiley |
| 9,700,356 B2 | 7/2017 | Donner et al. |
| 9,744,051 B2 | 8/2017 | Biedermann et al. |
| 9,757,235 B2 | 9/2017 | Hunt et al. |
| 9,782,270 B2 | 10/2017 | Wickham |
| 9,788,967 B2 | 10/2017 | Jo |
| 9,814,578 B1 | 11/2017 | Gotfried |
| 9,907,670 B2 | 3/2018 | DeRidder et al. |
| 9,918,849 B2 | 3/2018 | Morris et al. |
| 9,931,209 B2 | 4/2018 | Gotfried |
| 9,987,051 B2 | 6/2018 | Nunley et al. |
| 9,987,137 B2 | 6/2018 | Hunt et al. |
| 9,999,516 B2 | 6/2018 | Hunt |
| 10,004,546 B2 | 6/2018 | Gotfried |
| 10,016,279 B1 | 7/2018 | Castro |
| 10,058,433 B2 | 8/2018 | Lechmann et al. |
| 10,064,737 B2 | 9/2018 | Tsai et al. |
| 10,098,754 B2 | 10/2018 | Larsson |
| 10,117,746 B2 | 11/2018 | Cordaro |
| 10,143,569 B2 | 12/2018 | Weiman et al. |
| 10,154,913 B2 | 12/2018 | Steinmann et al. |
| 10,159,580 B2 | 12/2018 | Guizzardi et al. |
| 10,182,923 B2 | 1/2019 | Willis et al. |
| 10,194,962 B2 | 2/2019 | Schneider et al. |
| 10,195,524 B2 | 2/2019 | DeRidder et al. |
| 10,213,317 B2 | 2/2019 | Bishop et al. |
| 10,226,357 B2 | 3/2019 | Ries |
| 10,254,274 B2 | 4/2019 | Miklas et al. |
| 10,265,189 B2 | 4/2019 | Melkent et al. |
| 10,271,958 B2 | 4/2019 | Schaufler et al. |
| 10,278,833 B2 | 5/2019 | Howard et al. |
| 10,278,834 B2 | 5/2019 | Howard et al. |
| 10,357,377 B2 | 7/2019 | Nyahay et al. |
| 10,368,997 B2 | 8/2019 | Jones et al. |
| 10,369,009 B2 | 8/2019 | Joly et al. |
| 10,413,427 B2 | 9/2019 | Trieu |
| 10,433,977 B2 | 10/2019 | Lechmann et al. |
| 10,433,979 B2 | 10/2019 | Morris et al. |
| 10,449,051 B2 | 10/2019 | Hamzey et al. |
| 10,449,055 B2 | 10/2019 | McJunkin |
| 10,449,058 B2 | 10/2019 | Lechmann et al. |
| 10,478,312 B2 | 11/2019 | McShane, III et al. |
| D870,288 S | 12/2019 | Dang et al. |
| 10,492,921 B2 | 12/2019 | McShane, III et al. |
| 10,507,118 B2 | 12/2019 | Afzal |
| 10,512,549 B2 | 12/2019 | Bishop et al. |
| 10,517,739 B2 | 12/2019 | Ryan |
| 10,524,926 B2 | 1/2020 | Jasinski |
| 10,524,927 B2 | 1/2020 | Ryan |
| 10,524,929 B2 | 1/2020 | Shoshtaev |
| 10,525,688 B2 | 1/2020 | O'Neill et al. |
| 10,531,962 B2 | 1/2020 | Petersheim et al. |
| 10,537,666 B2 | 1/2020 | Paddock |
| 10,555,819 B2 | 2/2020 | Miccio |
| 10,561,456 B2 | 2/2020 | Cawley et al. |
| 10,575,965 B2 | 3/2020 | Kim et al. |
| 10,588,755 B2 | 3/2020 | Vogt et al. |
| 10,617,532 B2 | 4/2020 | Mazur et al. |
| 10,624,760 B2 | 4/2020 | Mirda et al. |
| 10,660,763 B2 | 5/2020 | Wilson et al. |
| 10,660,764 B2 | 5/2020 | Maglaras et al. |
| 10,667,924 B2 | 6/2020 | Nyahay et al. |
| 10,675,158 B2 | 6/2020 | Unger et al. |
| 10,675,385 B2 | 6/2020 | Barbas et al. |
| 10,682,238 B2 | 6/2020 | Petersheim et al. |
| 10,695,192 B2 | 6/2020 | Bishop et al. |
| 10,709,570 B2 | 7/2020 | Stauffer et al. |
| 10,716,678 B2 | 7/2020 | Stampfli et al. |
| 10,722,378 B2 | 7/2020 | Davis et al. |
| 10,744,001 B2 | 8/2020 | Sack |
| 10,744,003 B2 | 8/2020 | Ryan et al. |
| 10,765,530 B2 | 9/2020 | Steinmann et al. |
| 10,772,732 B1 | 9/2020 | Miller et al. |
| D898,197 S | 10/2020 | Cain |
| 10,835,388 B2 | 11/2020 | Milz et al. |
| 10,849,756 B2 | 12/2020 | Hunt et al. |
| 10,856,999 B2 | 12/2020 | Bishop et al. |
| 10,940,019 B2 | 3/2021 | Vishnubhotla et al. |
| D920,515 S | 5/2021 | Miller et al. |
| D920,516 S | 5/2021 | Miller et al. |
| 11,026,798 B1 | 6/2021 | Miller et al. |

(56) References Cited

U.S. PATENT DOCUMENTS

| | | |
|---|---|---|
| 11,033,394 B2 | 6/2021 | Hamzey et al. |
| 11,065,039 B2 | 7/2021 | McCormack |
| 11,147,679 B2 | 10/2021 | Kowalczyk et al. |
| 11,160,668 B2 | 11/2021 | Nyahay et al. |
| D942,011 S | 1/2022 | Cain |
| 11,213,405 B2 | 1/2022 | Bishop et al. |
| D942,623 S | 2/2022 | Cain |
| D942,624 S | 2/2022 | Cain |
| D944,400 S | 2/2022 | Cain |
| 11,273,048 B2 | 3/2022 | Cain et al. |
| 11,452,611 B2 | 9/2022 | McShane, III et al. |
| 2001/0014826 A1 | 8/2001 | Biedermann et al. |
| 2001/0032018 A1 | 10/2001 | Castro et al. |
| 2002/0052656 A1 | 5/2002 | Michelson |
| 2002/0120334 A1 | 8/2002 | Crozet |
| 2002/0123750 A1 | 9/2002 | Eisermann et al. |
| 2002/0183847 A1 | 12/2002 | Lieberman |
| 2003/0003127 A1 | 1/2003 | Brown et al. |
| 2003/0060825 A1 | 3/2003 | Alfaro |
| 2003/0078660 A1 | 4/2003 | Clifford et al. |
| 2003/0083746 A1 | 5/2003 | Kuslich |
| 2003/0109928 A1 | 6/2003 | Pasquet |
| 2003/0181913 A1 | 9/2003 | Lieberman |
| 2003/0236571 A1 | 12/2003 | Ralph |
| 2004/0059419 A1 | 3/2004 | Michelson |
| 2004/0082953 A1 | 4/2004 | Petit |
| 2004/0122518 A1 | 6/2004 | Rhoda |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2005/0015154 A1 | 1/2005 | Lindsey et al. |
| 2005/0027364 A1 | 2/2005 | Kim |
| 2005/0143733 A1 | 6/2005 | Petit |
| 2005/0177238 A1 | 8/2005 | Khandkar et al. |
| 2005/0222681 A1 | 10/2005 | Richley et al. |
| 2005/0251260 A1 | 11/2005 | Gerber et al. |
| 2005/0278027 A1 | 12/2005 | Hyde, Jr. |
| 2005/0278028 A1 | 12/2005 | Mujwid |
| 2006/0041262 A1 | 2/2006 | Calvert et al. |
| 2006/0052872 A1 | 3/2006 | Studer |
| 2006/0052873 A1 | 3/2006 | Buck |
| 2006/0058881 A1 | 3/2006 | Trieu |
| 2006/0100706 A1 | 5/2006 | Shadduck et al. |
| 2006/0147332 A1 | 7/2006 | Jones et al. |
| 2006/0212118 A1 | 9/2006 | Abernathie |
| 2006/0217806 A1 | 9/2006 | Peterman |
| 2006/0293753 A1 | 12/2006 | Thramann |
| 2007/0027544 A1 | 2/2007 | McCord et al. |
| 2007/0179610 A1 | 8/2007 | Biedermann et al. |
| 2007/0198090 A1 | 8/2007 | Abdou |
| 2007/0260324 A1 | 11/2007 | Joshi et al. |
| 2008/0071356 A1 | 3/2008 | Greenhalgh |
| 2008/0167686 A1 | 7/2008 | Trieu |
| 2008/0183204 A1 | 7/2008 | Greenhalgh et al. |
| 2008/0255666 A1 | 10/2008 | Fisher |
| 2008/0288083 A1 | 11/2008 | Axelsson et al. |
| 2008/0300602 A1 | 12/2008 | Schmitt et al. |
| 2008/0306595 A1 | 12/2008 | McLeod et al. |
| 2008/0312742 A1 | 12/2008 | Abernathie |
| 2009/0030520 A1 | 1/2009 | Biedermann |
| 2009/0036985 A1 | 2/2009 | Whiting |
| 2009/0048675 A1 | 2/2009 | Bhatnagar et al. |
| 2009/0048678 A1 | 2/2009 | Saal et al. |
| 2009/0062917 A1 | 3/2009 | Foley et al. |
| 2009/0112321 A1 | 4/2009 | Kitchen |
| 2009/0149958 A1 | 6/2009 | Prewett et al. |
| 2009/0248162 A1 | 10/2009 | Peckham |
| 2010/0016974 A1 | 1/2010 | Janowski |
| 2010/0036498 A1 | 2/2010 | McDevitt |
| 2010/0057216 A1 | 3/2010 | Gannoe et al. |
| 2010/0137990 A1 | 6/2010 | Apatsidis |
| 2010/0145451 A1 | 6/2010 | Dee |
| 2010/0152856 A1 | 6/2010 | Overes |
| 2010/0161061 A1 | 6/2010 | Hunt |
| 2010/0185292 A1 | 7/2010 | Hochschuler |
| 2010/0228299 A1 | 9/2010 | Zrinski et al. |
| 2010/0286778 A1 | 11/2010 | Eisermann et al. |
| 2011/0015741 A1 | 1/2011 | Melkent et al. |
| 2011/0029085 A1 | 2/2011 | Hynes |
| 2011/0035019 A1 | 2/2011 | Goswami et al. |
| 2011/0066192 A1 | 3/2011 | Frasier et al. |
| 2011/0166660 A1 | 7/2011 | Laurence |
| 2011/0190888 A1 | 8/2011 | Bertele |
| 2011/0190895 A1 | 8/2011 | Segal et al. |
| 2011/0208311 A1 | 8/2011 | Janowski |
| 2011/0230970 A1 | 9/2011 | Lynn |
| 2011/0245926 A1 | 10/2011 | Kitchen |
| 2011/0270401 A1 | 11/2011 | McKay |
| 2011/0301709 A1 | 12/2011 | Kraus et al. |
| 2011/0313528 A1 | 12/2011 | Laubert |
| 2011/0313532 A1 | 12/2011 | Hunt |
| 2012/0010472 A1 | 1/2012 | Spann |
| 2012/0010717 A1 | 1/2012 | Spann |
| 2012/0150300 A1 | 6/2012 | Nihalani |
| 2012/0158143 A1 | 6/2012 | Shapiro |
| 2012/0191188 A1 | 7/2012 | Huang |
| 2012/0191189 A1 | 7/2012 | Huang |
| 2012/0220934 A1 | 8/2012 | Diener et al. |
| 2012/0232654 A1 | 9/2012 | Sharp et al. |
| 2012/0239150 A1 | 9/2012 | Ullrich |
| 2012/0285836 A1 | 11/2012 | von Oepen |
| 2012/0296431 A1 | 11/2012 | Kim |
| 2013/0030529 A1 | 1/2013 | Hunt |
| 2013/0096685 A1 | 4/2013 | Ciupik |
| 2013/0116793 A1 | 5/2013 | Kloss |
| 2013/0123935 A1 | 5/2013 | Hunt et al. |
| 2013/0158672 A1 | 6/2013 | Hunt |
| 2013/0184826 A1 | 7/2013 | Thaiyananthan |
| 2013/0190880 A1 | 7/2013 | Schaller |
| 2013/0021288 A1 | 8/2013 | Fonte |
| 2013/0218288 A1 | 8/2013 | Fonte |
| 2013/0226300 A1 | 8/2013 | Chataigner |
| 2013/0304211 A1 | 11/2013 | Trautwein et al. |
| 2014/0018814 A1 | 1/2014 | Gillard et al. |
| 2014/0018948 A1* | 1/2014 | Metzger ............... G16Z 99/00 700/98 |
| 2014/0052260 A1 | 2/2014 | McKenny |
| 2014/0058513 A1 | 2/2014 | Gahman et al. |
| 2014/0107785 A1 | 4/2014 | Geisler |
| 2014/0107786 A1 | 4/2014 | Geisler et al. |
| 2014/0114418 A1 | 4/2014 | Landry |
| 2014/0121776 A1 | 5/2014 | Hunt |
| 2014/0142707 A1 | 5/2014 | Compton et al. |
| 2014/0172111 A1 | 6/2014 | Lang et al. |
| 2014/0195005 A1 | 7/2014 | McKay |
| 2014/0228956 A1 | 8/2014 | Weiman |
| 2014/0228960 A1 | 8/2014 | Forterre |
| 2014/0243980 A1 | 8/2014 | Sack et al. |
| 2014/0249631 A1 | 9/2014 | Weiman |
| 2014/0277457 A1 | 9/2014 | Yeung et al. |
| 2014/0277464 A1 | 9/2014 | Richter et al. |
| 2014/0277569 A1 | 9/2014 | Lange |
| 2014/0288649 A1 | 9/2014 | Hunt |
| 2014/0288650 A1 | 9/2014 | Hunt |
| 2014/0303736 A1 | 10/2014 | Roussouly |
| 2014/0303745 A1 | 10/2014 | Anderson et al. |
| 2014/0309743 A1 | 10/2014 | Falahee |
| 2014/0336771 A1 | 11/2014 | Zambiasi |
| 2014/0358246 A1 | 12/2014 | Levy et al. |
| 2015/0045903 A1 | 2/2015 | Neal |
| 2015/0112351 A1 | 4/2015 | Hsu |
| 2015/0127106 A1 | 5/2015 | Partee et al. |
| 2015/0173910 A1 | 6/2015 | Siegal |
| 2015/0223951 A1 | 8/2015 | Bae et al. |
| 2015/0282944 A1 | 10/2015 | Guizzardi et al. |
| 2016/0008149 A1 | 1/2016 | Hsiao et al. |
| 2016/0015437 A1 | 1/2016 | Elleby et al. |
| 2016/0022430 A1 | 1/2016 | Wickham |
| 2016/0081809 A1 | 3/2016 | Schneider et al. |
| 2016/0166284 A1 | 6/2016 | Hacking et al. |
| 2016/0184103 A1 | 6/2016 | Fonte et al. |
| 2016/0193057 A1 | 7/2016 | Rhoda |
| 2016/0206439 A1 | 7/2016 | To et al. |
| 2016/0206440 A1 | 7/2016 | DeRidder et al. |

(56) References Cited

U.S. PATENT DOCUMENTS

| | | |
|---|---|---|
| 2016/0262903 A1 | 9/2016 | West |
| 2016/0270920 A1 | 9/2016 | Dawson et al. |
| 2016/0287388 A1 | 10/2016 | Hunt et al. |
| 2016/0287405 A1 | 10/2016 | Hunt et al. |
| 2016/0310294 A1 | 10/2016 | McConnell |
| 2016/0317320 A1 | 11/2016 | Ahn |
| 2016/0324656 A1 | 11/2016 | Morris et al. |
| 2016/0374727 A1 | 12/2016 | Greenhalgh et al. |
| 2017/0007409 A1 | 1/2017 | Mauldin et al. |
| 2017/0014235 A1 | 1/2017 | Jones et al. |
| 2017/0020685 A1 | 1/2017 | Geisler et al. |
| 2017/0042697 A1 | 2/2017 | McShane, III et al. |
| 2017/0049488 A1 | 2/2017 | Vestgaarden |
| 2017/0095337 A1 | 4/2017 | Pasini et al. |
| 2017/0095352 A1 | 4/2017 | Bruffey |
| 2017/0100167 A1 | 4/2017 | Lange et al. |
| 2017/0135706 A1 | 5/2017 | Frey et al. |
| 2017/0135733 A1 | 5/2017 | Donner et al. |
| 2017/0143383 A1 | 5/2017 | Ingalhalikar et al. |
| 2017/0151005 A1 | 6/2017 | Warren et al. |
| 2017/0156740 A9 | 6/2017 | Stark |
| 2017/0156766 A1 | 6/2017 | Anderson et al. |
| 2017/0156878 A1 | 6/2017 | Tsai |
| 2017/0156879 A1 | 6/2017 | Janowski |
| 2017/0156880 A1 | 6/2017 | Halverson et al. |
| 2017/0164979 A1 | 6/2017 | Donner et al. |
| 2017/0181784 A1 | 6/2017 | Li |
| 2017/0182222 A1 | 6/2017 | Paddock |
| 2017/0196693 A1 | 7/2017 | Jurick et al. |
| 2017/0216034 A1 | 8/2017 | Daniel |
| 2017/0216035 A1 | 8/2017 | Hunt |
| 2017/0239064 A1 | 8/2017 | Cordaro |
| 2017/0239066 A1 | 8/2017 | Walsh et al. |
| 2017/0258606 A1 | 9/2017 | Afzal |
| 2017/0319353 A1 | 11/2017 | Greenhalgh et al. |
| 2017/0348107 A1 | 12/2017 | Lee et al. |
| 2017/0348115 A1 | 12/2017 | Greenhalgh |
| 2018/0064540 A1 | 3/2018 | Hunt et al. |
| 2018/0085230 A1 | 3/2018 | Hunt |
| 2018/0110626 A1 | 4/2018 | McShane, III |
| 2018/0161477 A1 | 6/2018 | Nies |
| 2018/0221156 A1 | 8/2018 | Jones |
| 2018/0243104 A1 | 8/2018 | Garonzik |
| 2018/0256336 A1 | 9/2018 | Mueller et al. |
| 2018/0256352 A1 | 9/2018 | Nyahay et al. |
| 2018/0280139 A1 | 10/2018 | Jones |
| 2018/0289503 A1 | 10/2018 | Knapp |
| 2018/0296343 A1 | 10/2018 | Wei |
| 2018/0296350 A1 | 10/2018 | Hamzey et al. |
| 2018/0326493 A1 | 11/2018 | Gallagher et al. |
| 2018/0333272 A1 | 11/2018 | Mirda |
| 2018/0338838 A1 | 11/2018 | Cryder et al. |
| 2018/0368981 A1 | 12/2018 | Mattes et al. |
| 2018/0368991 A1 | 12/2018 | Levieux |
| 2019/0000636 A1 | 1/2019 | Kim et al. |
| 2019/0015209 A1 | 1/2019 | Seifert et al. |
| 2019/0038428 A1 | 2/2019 | Stauffer |
| 2019/0060079 A1 | 2/2019 | Unis et al. |
| 2019/0060083 A1 | 2/2019 | Weiman et al. |
| 2019/0076266 A1 | 3/2019 | Trudeau et al. |
| 2019/0083282 A1 | 3/2019 | Roeder et al. |
| 2019/0091027 A1 | 3/2019 | Asaad et al. |
| 2019/0133769 A1 | 5/2019 | Tetsworth et al. |
| 2019/0151109 A1 | 5/2019 | Arnin |
| 2019/0151113 A1 | 5/2019 | Sack |
| 2019/0159818 A1 | 5/2019 | Schneider et al. |
| 2019/0183653 A1 | 6/2019 | Gregersen et al. |
| 2019/0224023 A1 | 7/2019 | Howard et al. |
| 2019/0254840 A1 | 8/2019 | Gray et al. |
| 2019/0262139 A1 | 8/2019 | Wolters |
| 2019/0274841 A1 | 9/2019 | Hawkes et al. |
| 2019/0298542 A1 | 10/2019 | Kioss |
| 2019/0307574 A1 | 10/2019 | Nyahay et al. |
| 2019/0314169 A1 | 10/2019 | Patel et al. |
| 2019/0328546 A1 | 10/2019 | Palagi et al. |
| 2019/0336305 A1 | 11/2019 | Joly et al. |
| 2019/0343645 A1 | 11/2019 | Miccio et al. |
| 2019/0358058 A1 | 11/2019 | Trieu |
| 2019/0388238 A1 | 12/2019 | Lechmann et al. |
| 2020/0000603 A1 | 1/2020 | McJunkin |
| 2020/0036011 A1 | 1/2020 | Numata et al. |
| 2020/0038197 A1 | 2/2020 | Morris et al. |
| 2020/0038198 A1 | 2/2020 | Miccio |
| 2020/0086625 A1 | 3/2020 | O'Neill et al. |
| 2020/0113707 A1 | 4/2020 | Petersheim et al. |
| 2020/0113709 A1 | 4/2020 | Hsieh |
| 2020/0121470 A1 | 4/2020 | Moore et al. |
| 2020/0138595 A1 | 5/2020 | Shoshtaev et al. |
| 2020/0146842 A1 | 5/2020 | Jasinski |
| 2020/0155326 A1 | 5/2020 | Hunt |
| 2020/0179128 A1 | 6/2020 | Stalcup et al. |
| 2020/0179133 A1 | 6/2020 | Ryan |
| 2020/0188120 A1 | 6/2020 | Hamzey et al. |
| 2020/0188129 A1 | 6/2020 | McShane, III et al. |
| 2020/0188132 A1 | 6/2020 | Ryan |
| 2020/0188133 A1 | 6/2020 | McShane, III et al. |
| 2020/0190680 A1 | 6/2020 | Numata et al. |
| 2020/0197189 A1 | 6/2020 | Mazur et al. |
| 2020/0214852 A1 | 7/2020 | Tipping et al. |
| 2020/0222201 A1 | 7/2020 | Mirda et al. |
| 2020/0229940 A1 | 7/2020 | Bishop et al. |
| 2020/0229945 A1 | 7/2020 | Levieux |
| 2020/0237526 A1 | 7/2020 | Wilson et al. |
| 2020/0246160 A1 | 8/2020 | Zappacosta et al. |
| 2020/0261243 A1 | 8/2020 | Unger et al. |
| 2020/0268523 A1 | 8/2020 | Barthold et al. |
| 2020/0276019 A1 | 9/2020 | Shetty et al. |
| 2020/0281727 A1 | 9/2020 | Dang et al. |
| 2020/0297494 A1 | 9/2020 | Hunt et al. |
| 2020/0297505 A1 | 9/2020 | McLaughlin |
| 2020/0315812 A1 | 10/2020 | Davis et al. |
| 2020/0323645 A1 | 10/2020 | Northcutt et al. |
| 2020/0337851 A1 | 10/2020 | Stampfli et al. |
| 2020/0337855 A1 | 10/2020 | Stauffer et al. |
| 2020/0337856 A1 | 10/2020 | Moore et al. |
| 2020/0345506 A1 | 11/2020 | Ryan et al. |
| 2020/0352735 A1 | 11/2020 | Afzal |
| 2020/0375757 A1 | 12/2020 | Sack |
| 2020/0375758 A1 | 12/2020 | Northcutt et al. |
| 2020/0376174 A1 | 12/2020 | Melkent et al. |
| 2021/0022882 A1 | 1/2021 | Dang et al. |
| 2021/0046211 A1 | 2/2021 | Deisinger et al. |
| 2021/0069383 A1 | 3/2021 | Yamaguchi et al. |
| 2021/0085481 A1 | 3/2021 | Cain et al. |
| 2021/0307909 A1 | 10/2021 | Hamzey et al. |
| 2022/0047398 A1 | 2/2022 | Nyahay et al. |
| 2022/0071777 A1 | 3/2022 | Cain et al. |
| 2022/0117753 A1 | 4/2022 | Rucker et al. |

FOREIGN PATENT DOCUMENTS

| | | |
|---|---|---|
| CN | 204931903 | 1/2016 |
| CN | 110179570 B | 8/2021 |
| DE | 19722389 | 12/1998 |
| EP | 3064175 | 9/2016 |
| EP | 3494931 | 6/2019 |
| EP | 3517078 | 7/2019 |
| EP | 3603580 | 2/2020 |
| FR | 2815846 | 5/2002 |
| FR | 2955025 | 7/2011 |
| JP | H05261146 | 10/1993 |
| JP | H09503416 | 9/1997 |
| JP | 2001523129 | 11/2001 |
| JP | 20010523129 | 11/2001 |
| JP | 2004-510494 | 4/2004 |
| JP | 2006515194 | 5/2006 |
| JP | 2009-505686 | 2/2009 |
| JP | 2009504332 | 2/2009 |
| JP | 4313005 | 8/2009 |
| JP | 2010137069 | 6/2010 |
| JP | 201115959 | 1/2011 |
| JP | 2012-501236 | 1/2012 |
| JP | 2012501236 | 1/2012 |
| JP | 20120501236 | 1/2012 |

(56) References Cited

FOREIGN PATENT DOCUMENTS

| | | |
|---|---|---|
| JP | 5328051 | 10/2013 |
| JP | 5455020 | 3/2014 |
| JP | 2014-151209 | 8/2014 |
| JP | 2015-502192 | 1/2015 |
| JP | 2015502192 | 1/2015 |
| JP | 5684177 | 3/2015 |
| JP | 2015529150 | 10/2015 |
| JP | A2018-516646 | 6/2018 |
| JP | 2019034071 | 3/2019 |
| JP | 2019041886 | 3/2019 |
| JP | 2019180797 | 10/2019 |
| JP | 2019201688 | 11/2019 |
| JP | 6700135 | 5/2020 |
| JP | 2020199326 | 12/2020 |
| JP | 2021016498 | 2/2021 |
| WO | WO 9510248 | 4/1995 |
| WO | WO 9848738 | 11/1998 |
| WO | WO 9852498 | 11/1998 |
| WO | WO 0209625 | 2/2002 |
| WO | WO 0234168 | 5/2002 |
| WO | WO 03099160 | 12/2003 |
| WO | WO 2004084774 | 10/2004 |
| WO | WO 2005011523 | 2/2005 |
| WO | WO 2009051779 | 3/2006 |
| WO | WO 2007022194 | 2/2007 |
| WO | WO 2009051779 | 4/2009 |
| WO | WO 2010028056 | 3/2010 |
| WO | WO 2010097632 | 9/2010 |
| WO | WO 2013067528 | 5/2013 |
| WO | WO 2014052477 | 4/2014 |
| WO | 2014168631 | 10/2014 |
| WO | WO 2016044739 | 3/2016 |
| WO | WO 2016176496 | 11/2016 |
| WO | WO 2017100366 | 6/2017 |

OTHER PUBLICATIONS

Office Action dated May 5, 2017 in U.S. Appl. No. 15/141,655.
Office Action dated Nov. 1, 2018 in U.S. Appl. No. 15/885,418.
Final Office Action dated Feb. 25, 2019 in U.S. Appl. No. 15/885,418.
Office Action dated Nov. 2, 2021 in U.S. Appl. No. 16/593,101.
International Search Report and Written Opinion dated Aug. 19, 2016 in PCT/US2016/029865.
Office Action dated Apr. 3, 2019 in Chinese Application No. 201680039103.6.
Office Action dated Jun. 28, 2019 in European Application No. 16722008.6-1132.
Extended European Search Report dated Dec. 8, 2020 in European Application No. 20191843.0-1132.
ISO/ASTM 52900:2015€ Standard Terminology for Additive Manufacturing—General Principles—Terminology, 2017.
Office Action dated Mar. 5, 2020 in Japanese Application No. 2017-556733.
Office Action dated Sep. 2, 2021 in Japanese Application No. 2020-156918.
Notice of Decision to Grant a Patent dated Jul. 7, 2022 in Japanese Application No. 2020-156918.
Office Action dated Sep. 2, 2021 in Japanese Application No. 2020-156917.
Notice of Decision to Grant a Patent dated Jul. 7, 2022 in Japanese Application No. 2020-156917.
Office Action dated May 2, 2018 in U.S. Appl. No. 15/334,053.
Office Action dated Dec. 3, 2018 in U.S. Appl. No. 15/334,053.
Office Action dated Sep. 15, 2022 in U.S. Appl. No. 16/700,632.
Final Office Action dated Jun. 2, 2023 in U.S. Appl. No. 16/700,632.
International Search Report and Written Opinion dated Jan. 18, 2018.
"FDA Clears Camber Spine Technologies' 3D Printed SPIRA Open Matrix ALIF", Orthopedic Design & Technology, Aug. 15, 2017.
Supplemental Partial European Search Report dated May 15, 2020 in European Application No. 17866284.
Office Action dated Sep. 3, 2020 in European Application No. 17866284.
Office Action dated Mar. 23, 2022 in Chinese Application No. 2017800805197.
Office Action dated Mar. 25, 2021 in Japanese Application No. 2019-543187.
Office Action dated Aug. 5, 2021 in Japanese Application No. 2019-543187.
Office Action dated Jan. 12, 2022 in Japanese Application No. 2019-543187.
Preliminary Office Action dated Jan. 24, 2022 in Brazilian Application No. 112019008325-1.
Office Action dated Feb. 16, 2023 in Japanese Application No. 2021-197842.
Office Action dated Jul. 8, 2019 in U.S. Appl. No. 15/884,845.
Final Office Action dated Oct. 24, 2019 in U.S. Appl. No. 15/884,845.
International Search Report and Written Opinion dated Apr. 26, 2019 in PCT/US19/15946.
Office Action dated Dec. 9, 2021 in Japanese Application No. 2020-540800.
Office Action dated Apr. 27, 2023 in Japanese Application No. 2022-086976.
Office Action dated Nov. 5, 2020 in Australian Application No. 2019214987.
Office Action dated Oct. 15, 2021 in Australian Application No. 2019214987.
Office Action dated Mar. 27, 2023 in Australian Application No. 2022200666.
Office Action dated Oct. 25, 2018 in U.S. Appl. No. 15/791,279.
Final Office Action dated Mar. 1, 2019 in U.S. Appl. No. 15/791,279.
Office Action dated Mar. 1, 2022 in U.S. Appl. No. 16/659,011.
Final Office Action dated Jun. 21, 2022 in U.S. Appl. No. 16/659,011.
Office Action dated Feb. 27, 2023 in U.S. Appl. No. 16/659,011.
Office Action dated Apr. 20, 2023 in JP Application No. 2022-124717.

* cited by examiner

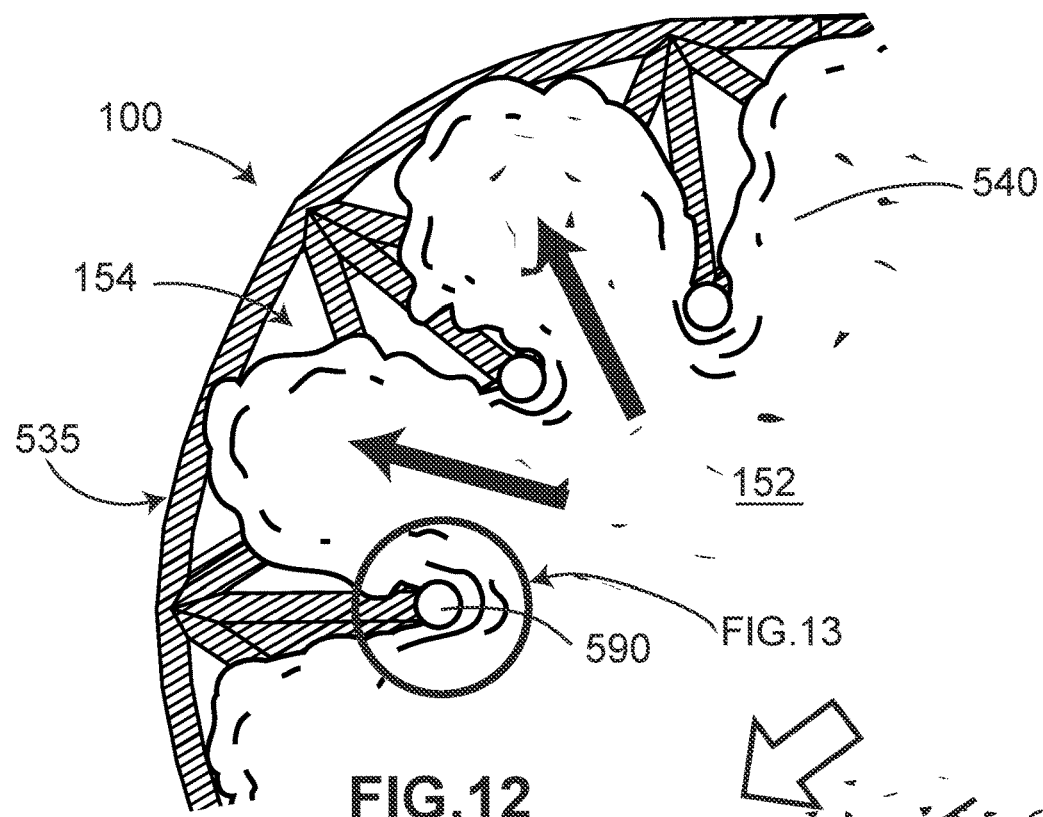
FIG.12
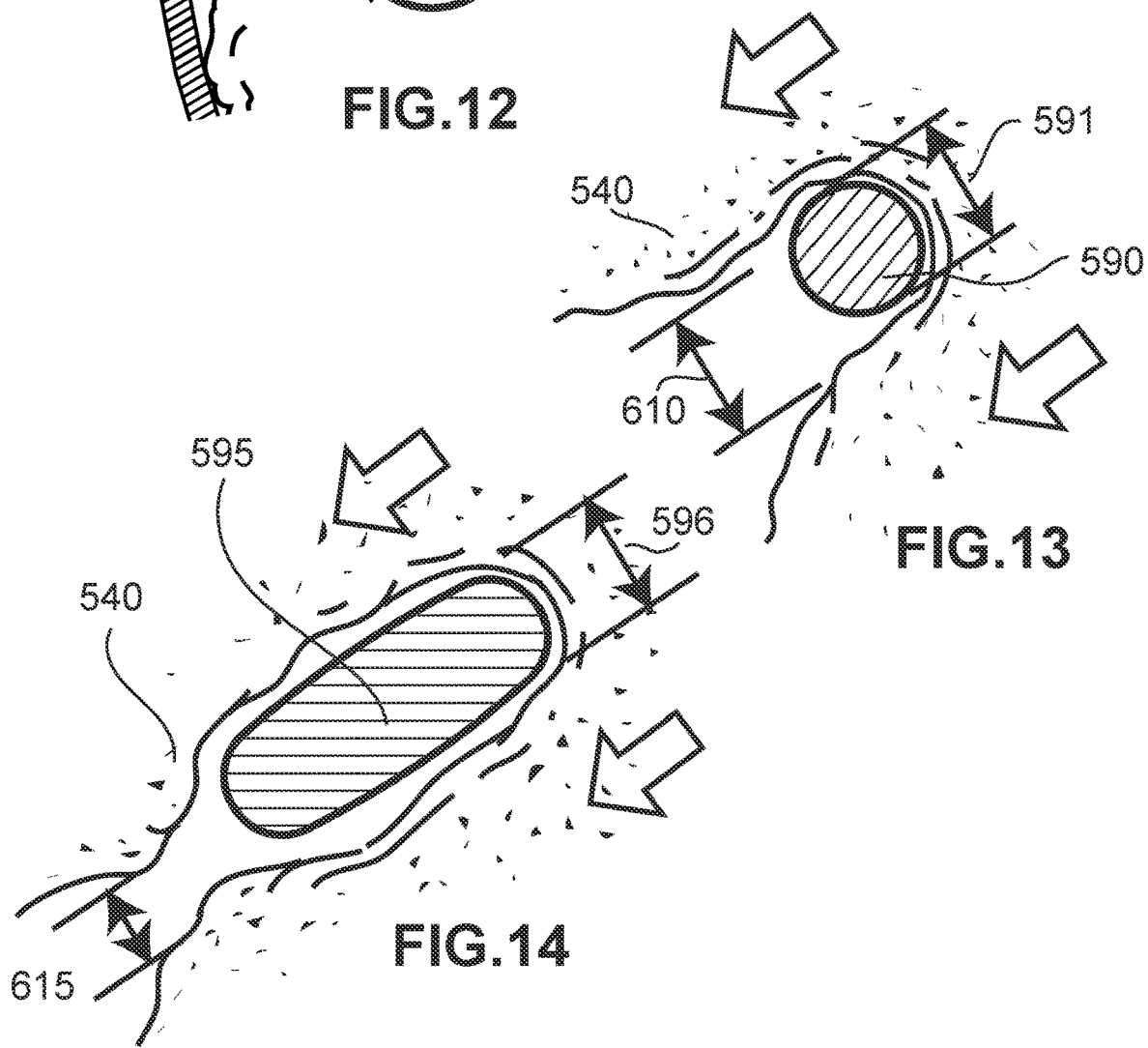
FIG.13
FIG.14

IMPLANT WITH IMPROVED FLOW CHARACTERISTICS

CROSS-REFERENCE TO RELATED APPLICATIONS

This application is a continuation of Sack, U.S. Patent Appl. Publ. No. 2019/0151113, published May 23, 2019, and entitled "Implant with Improved Flow Characteristics," the entire disclosure of which is incorporated herein by reference.

BACKGROUND

The embodiments are generally directed to implants for supporting bone growth in a patient.

A variety of different implants are used in the body. Implants used in the body to stabilize an area and promote bone ingrowth provide both stability (i.e., minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection, or tumor. The aim of the spinal fusion procedure is to reduce instability and thus pain.

In preparation for the spinal fusion, most of the intervertebral disc is removed. An implant, the spinal fusion cage, may be placed between the vertebrae to maintain spine alignment and disc height. The fusion, i.e., bone bridge, occurs between the endplates of the vertebrae.

Cage-style vertebral implants may be filled with bone graft material for implantation. Bone graft material can be a relatively viscous and even chunky material, and thus, can be difficult to introduce into the cage. In addition, different types of bone can have different structural properties. For example, cortical bone, also called compact bone or lamellar bone, forms the cortex, or outer shell, of most bones, including vertebrae. It is much denser than cancellous bone, as well as harder, stronger, and stiffer. Cortical bone contributes about 80% of the weight of a human skeleton. Cancellous bone, also called trabecular bone or spongy bone, has a higher surface area but is less dense than cortical bone, as well as softer, weaker, and less stiff. Cancellous bone typically occurs at the ends of long bones, proximal to joints and within the interior of vertebrae.

Because the same implant may support both cortical bone and cancellous bone, implants having consistent structural configuration and properties at bone confronting surfaces, may produce differing bone ingrowth results in different parts of the bone. For example, the cortical bone portion of vertebrae may respond differently to a spinal fusion implant than the cancellous bone core of the vertebrae.

It would be desirable to address these issues in intervertebral implants.

SUMMARY

The present disclosure is directed to intervertebral implants that include provisions to improve flow of bone graft material into the inner volume of the implant as well as structural configurations that vary across bone contacting surfaces of the implant. In particular, the disclosed implant may include a central portion that has a reduced density of trusses that form the cage. This may facilitate introduction of the bone graft material and also focus the structural support areas to the peripheral portion, which corresponds with the cortical bone area of vertebrae. In addition, the disclosed implant may include struts having particular orientations and arrangements that promote flow of bone graft material. For example, the disclosed implant may include struts having non-circular cross-sectional shapes, which may be oriented to facilitate and direct flow of bone graft material through the inner volume of the implant.

In one aspect, the present disclosure is directed to an intervertebral implant including a body formed as an open truss structure. The body may have a generally annular shape with a superior surface, an inferior surface, and a perimeter surface, the perimeter surface extending around an outer periphery of the body. The body has a central portion and a peripheral portion, the peripheral portion extending inward from the perimeter surface toward the central portion. The peripheral portion includes a first set of trusses having a first density of trusses, and the central portion includes a second set of trusses having a second density of trusses. The first density of trusses in the peripheral portion is greater than the second density of trusses in the central portion. The first set of trusses includes a first strut and a first node, and the second set of trusses includes a second strut, wherein the first node connects the first strut with the second strut.

In another aspect, an intervertebral implant includes an intervertebral implant comprising a body having an open truss structure, the body having a generally annular shape with opposing end surfaces, the opposing end surfaces including a superior surface and an inferior surface. The body may also have a perimeter surface, the perimeter surface extending around an outer periphery of the body. In addition, the body may have a central portion and a peripheral portion, the peripheral portion extending inward from the perimeter surface toward the central portion. Further, the peripheral portion may include a first set of trusses, the first set of trusses having a first density of trusses. Also, the central portion may include a second set of trusses, the second set of trusses having a second density of trusses. The first density of trusses in the peripheral portion is greater than the second density of trusses in the central portion, wherein the first set of trusses includes a first strut and a first node, wherein the second set of trusses includes a second strut, and wherein the first node connects the first strut with the second strut.

In another aspect, the present disclosure is directed to an intervertebral implant comprising a body having an open truss structure, the body having a generally annular shape with opposing end surfaces, the opposing end surfaces including a superior surface and an inferior surface. The body may also have a perimeter surface, the perimeter surface extending around an outer periphery of the body. In addition, the body may have a central portion and a peripheral portion, the peripheral portion extending inward from the perimeter surface toward the central portion, the central portion having a central axis. Also, the body may include a first strut disposed on the perimeter surface, and a second strut disposed inward of the perimeter surface so that the second strut is closer to the central axis than the first strut. The central axis and the second strut define a radial direction that extends from the central axis to the second strut. The second strut may have a non-circular cross-sectional shape with a cross-sectional length and a cross-sectional width, wherein the cross-sectional length is longer than the cross-sectional width, and wherein the cross-sectional length of the second strut extends along the radial direction.

In another aspect, the present disclosure is directed to a method of making an intervertebral implant having a body, the body having an open truss structure, the body including opposing end surfaces, and a perimeter surface, the perimeter surface extending around an outer periphery of the body; the body also including a central portion and a peripheral portion, the peripheral portion extending from the perimeter surface inward toward the central portion. The method of making may include additively manufacturing a first layer, the first layer being proximate a base plate; the first layer forming a part of the perimeter surface. The method may also include continuing to additively manufacture the body layer by layer wherein each successive layer is disposed further from the base plate than the previous layer so that the body is built vertically upward layer by layer. Further, the method may include additively manufacturing a lower peripheral portion, and additively manufacturing the peripheral portion and the central portion in the same layer, wherein this step occurs after the step of additively manufacturing the peripheral portion, and wherein less material is used to form the central portion than the peripheral portion so that a central truss structure is less dense than a peripheral truss structure. Also, the method may include additively manufacturing an upper peripheral portion.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

FIG. 12 is a schematic cutaway partial top view of an implant with the truss structure of the superior surface removed and bone graft material introduced from the central portion of the implant into the peripheral portion;

FIG. 13 is an enlarged schematic cutaway top view of an area associate with a single strut of the implant in FIG. 12;

FIG. 14 is an enlarged schematic cutaway top view of an area of a single strut of an implant wherein the strut has an oblong cross-sectional shape;

DETAILED DESCRIPTION

Any of the embodiments described herein may make use of any of the body/support structures, frames, plates, coils, or other structures disclosed in:

Hunt, U.S. Pat. No. 8,430,930, issued Apr. 30, 2013 and entitled "Truss Implant";

Hunt, U.S. Patent Appl. Publ. No. 2011/0313532, published Dec. 22, 2011 and entitled "Bone Implant Interface System and Method";

Hunt, U.S. Patent Appl. Publ. No. 2013/0030529, published Jan. 31, 2013 and entitled "Implant Interface system and method";

Hunt et al., U.S. Patent Appl. Publ. No. 2013/0123935, published May 16, 2013 and entitled "Method of Length Preservation During Bone Repair";

Hunt, U.S. Patent Appl. Publ. No. 2013/0218282, published Aug. 22, 2013 and entitled "Prosthetic Implant for Ball and Socket Joints and Method of Use";

Hunt et al., U.S. Pat. No. 9,271,845, issued Mar. 1, 2016 and entitled "Programmable Implants and Methods of Using Programmable Implants to Repair Bone Structures";

Hunt, U.S. Pat. No. 9,636,226, issued May 2, 2017 and entitled "Traumatic Bone Fracture Repair Systems and Methods";

Hunt, U.S. Patent Appl. Publ. No. 2014/0288650, published Sep. 25, 2014 and entitled "Motion Preservation Implant and Methods"; and Sack, U.S. Patent Appl. Publ. No. 2019/0151114, published May 23, 2019, and entitled "Implant with Improved Bone Contact."

The entire disclosures of the patents and publications listed above are incorporated herein by reference in their entirety.

For purposes of clarity, reference is made to various directional adjectives throughout the detailed description and in the claims. As used herein, the term "anterior" refers to a side or portion of an implant that is intended to be oriented toward the front of the human body when the implant has been placed in the body. Likewise, the term "posterior" refers to a side or portion of an implant that is intended to be oriented toward the back of the human body following implantation. In addition, the term "superior" refers to a side or portion of an implant that is intended to be oriented toward a top (e.g., the head) of the body while "inferior" refers to a side or portion of an implant that is intended to be oriented toward a bottom of the body. Reference is also made herein to "lateral" sides or portions of an implant, which are sides or portions facing along lateral directions of the body following implantation.

Implantation

Figure 1:
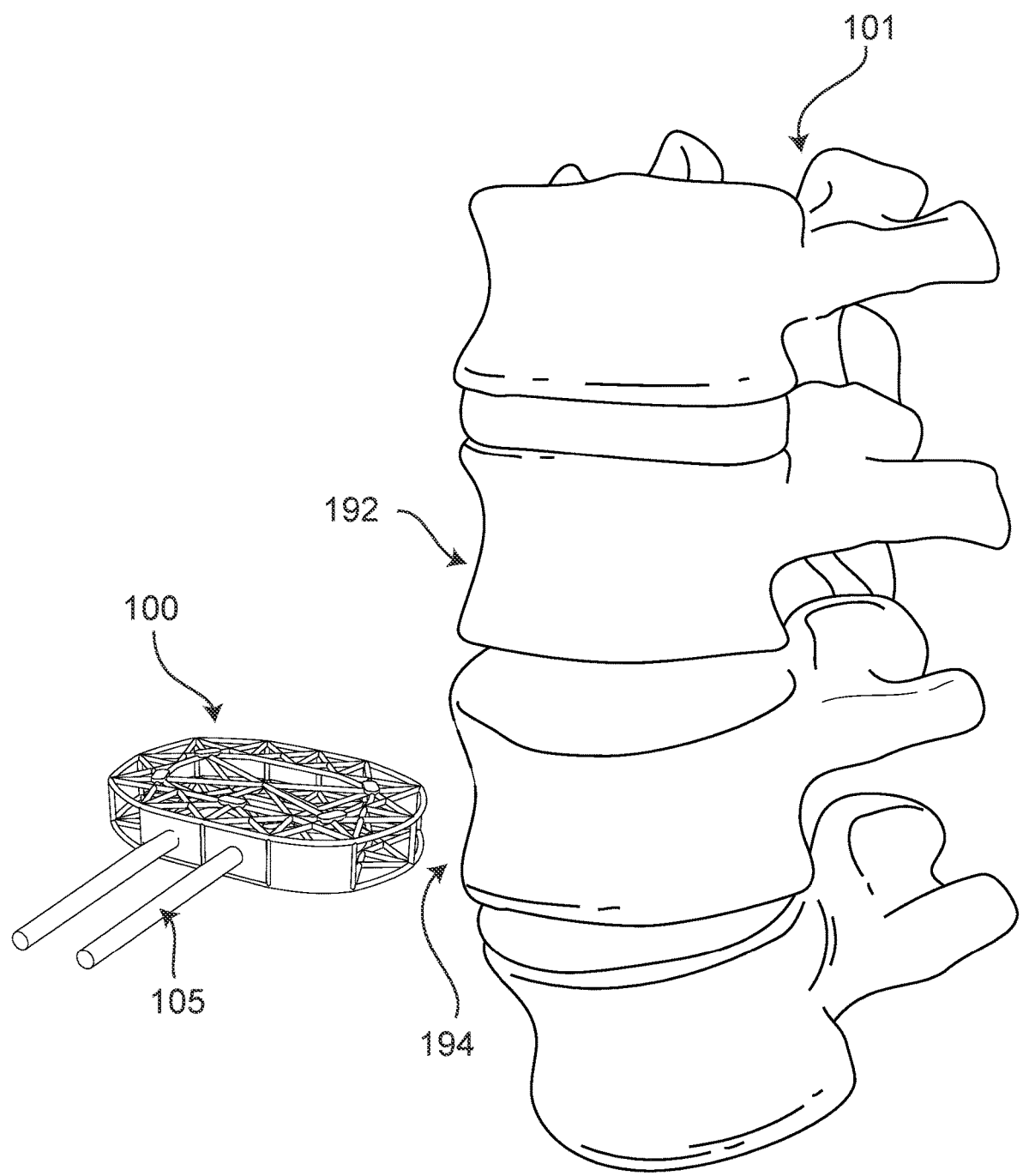
FIG. 1 is a schematic isometric view of a step of implanting a device into a spinal column, according to an exemplary disclosed embodiment.
Figure 2:
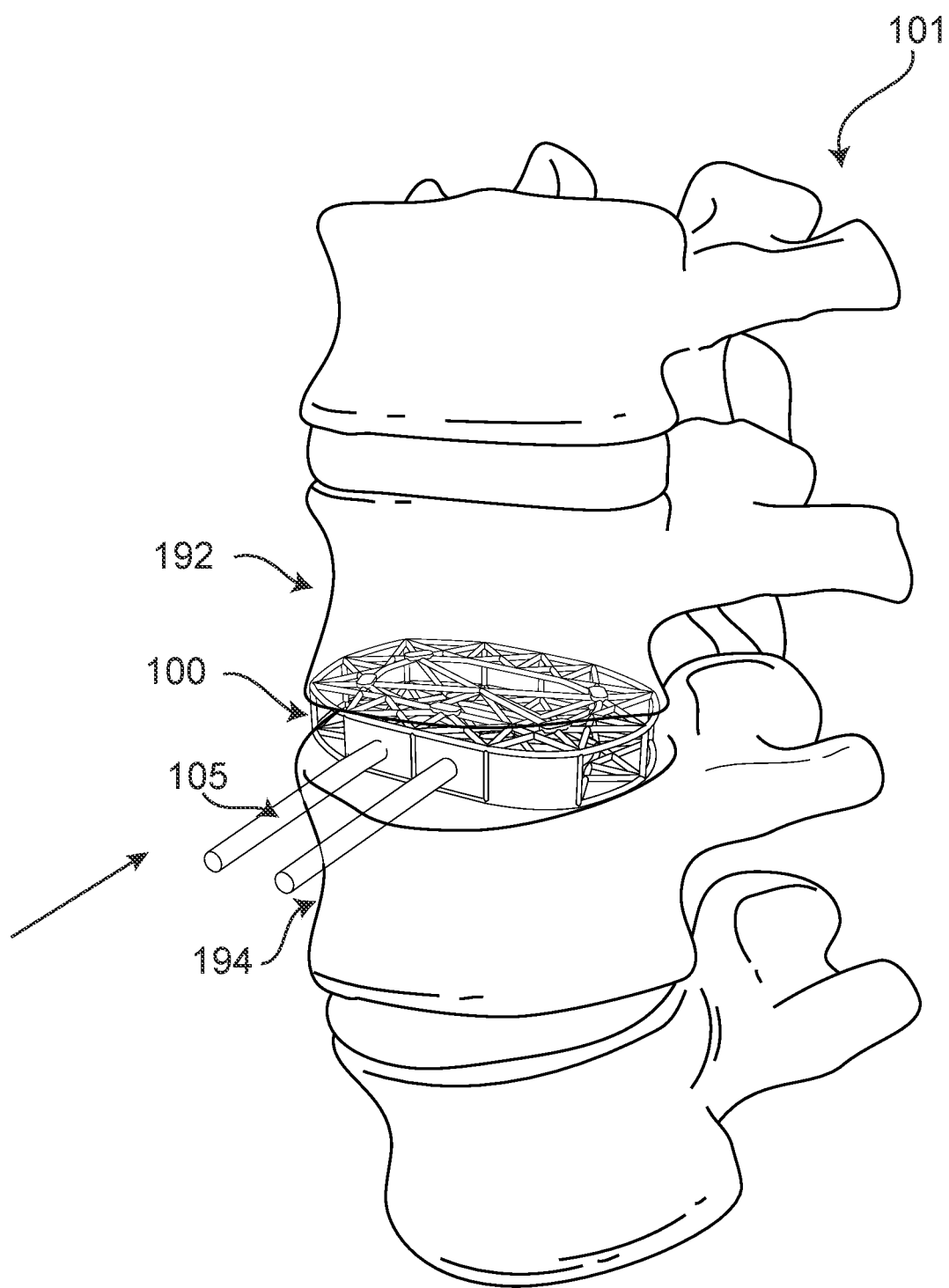
FIG. 2 is a schematic isometric view of a device implanted within a spinal column, according to an exemplary disclosed embodiment.

FIG. 1 is a schematic view of an embodiment of an implant 100. In some embodiments, implant 100 may be an intervertebral implant configured for placement between vertebral bodies of adjacent vertebrae. For purposes of context, implant 100 is shown adjacent to a portion of a spinal column 101. In FIG. 2, an embodiment of implant 100 is shown following insertion between two adjacent vertebrae (vertebra 192 and vertebra 194) within the spinal column 101. This insertion is facilitated by use of an insertion tool 105, which is shown schematically in FIGS. 1 and 2.

For purposes of this disclosure, implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, which is inserted between adjacent vertebrae to provide support and/or facilitate fusion between the vertebrae.

In some embodiments, implant 100 may be inserted using an anterior lumbar interbody fusion (ALIF) surgical procedure, where the disc space is fused by approaching the spine through the abdomen. In the ALIF approach, a three-inch to five-inch incision is typically made near the abdomen and the abdominal muscles are retracted to the side. In some cases, implant 100 can be inserted through a small incision in the front or anterior side of the body. In some cases, an anterior approach may afford improved exposure to the disc space to a surgeon. The anterior approach can allow a larger device to be used for the fusion, increasing the surface area for fusion to occur and allowing for more postoperative stability. An anterior approach often makes it possible to reduce some of the deformity caused by various conditions, such as isthmic spondylolisthesis. Insertion and placement of the implant can also re-establish the patient's normal sagittal alignment in some cases, giving individuals a more normal inward curve to their low back.

In some embodiments, the implant may be configured for insertion via a non-ALIF pathway. For example, in some embodiments, the implant may be configured for insertion via an oblique pathway, a lateral pathway, or any other pathway for inserting an intervertebral implant.

Introduction to Implant

Figure 3:
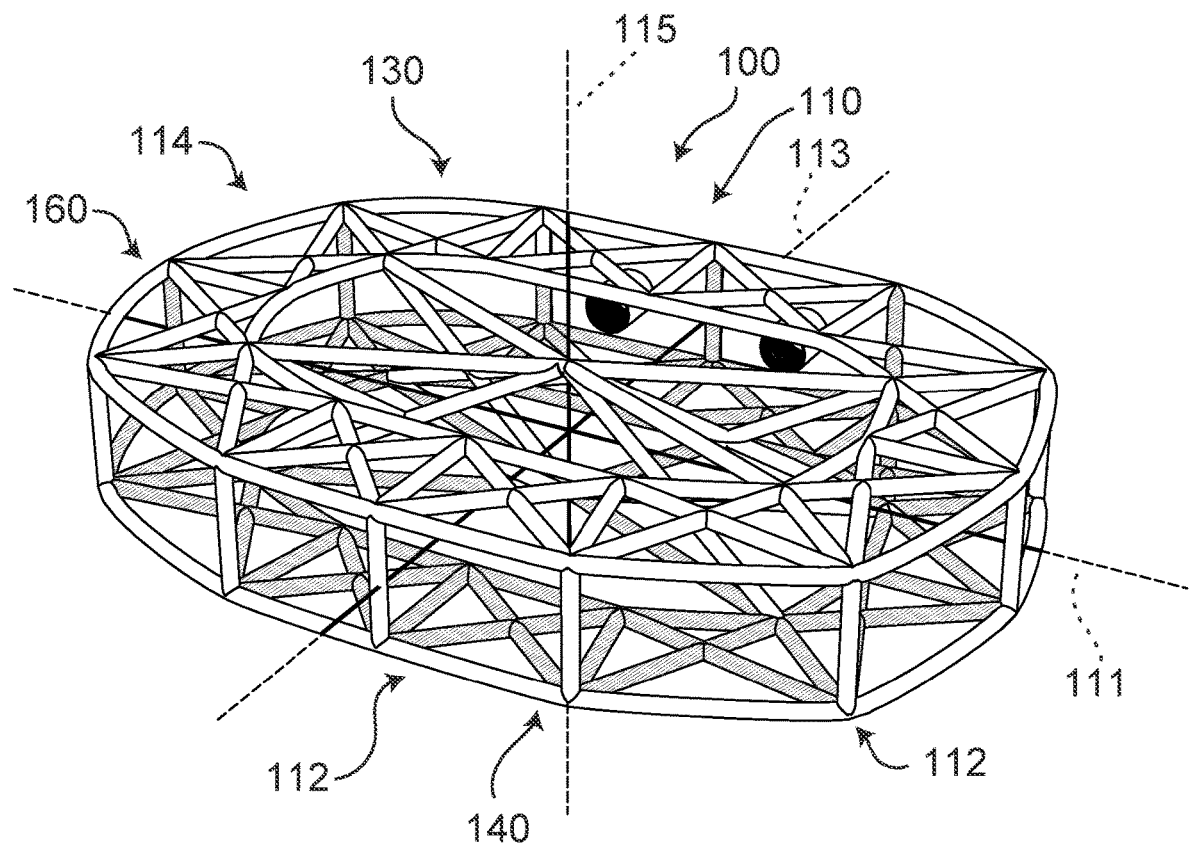
FIG. 3 is a schematic isometric view of an embodiment of an implant.
Figure 4:
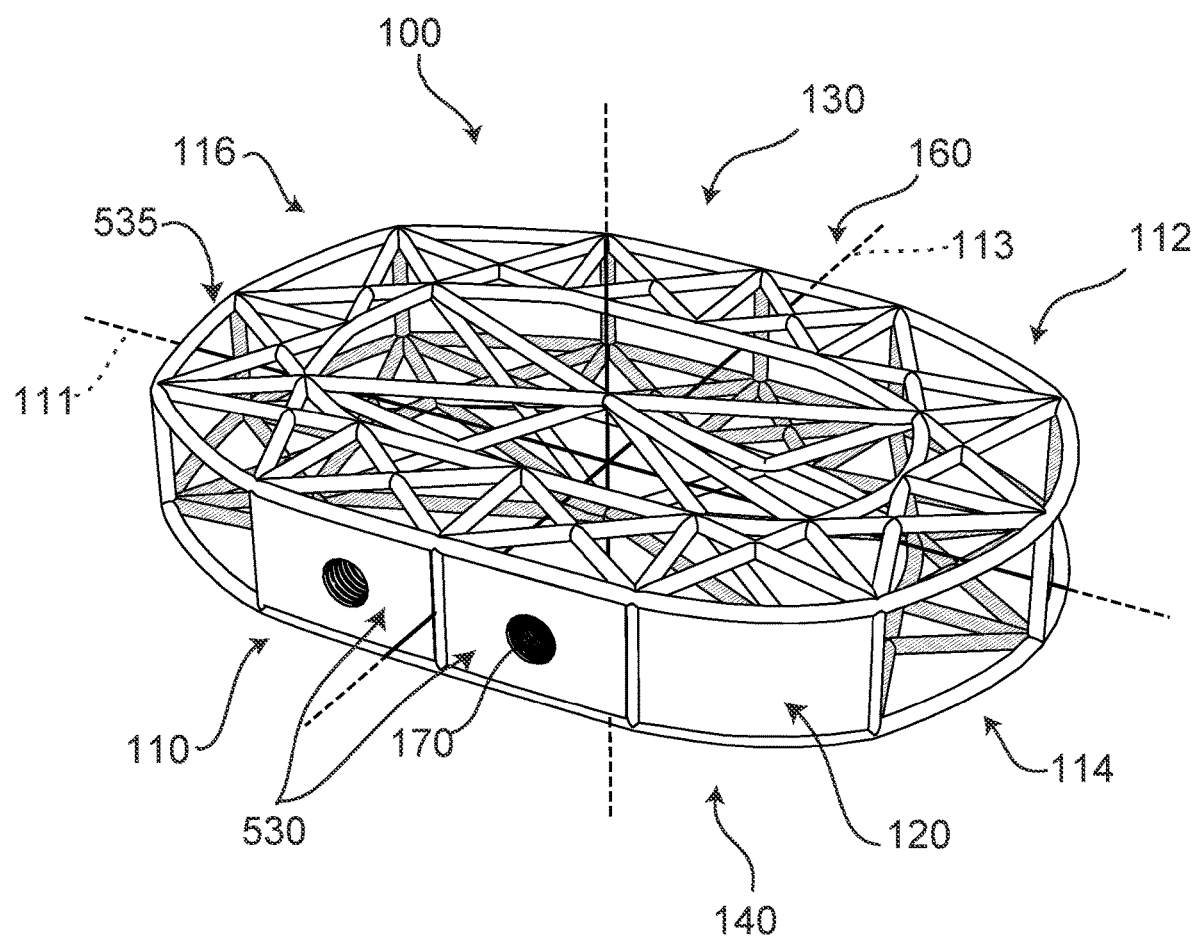
FIG. 4 is another schematic isometric view of the implant embodiment shown in FIG. 3.

FIGS. 3-4 illustrate isometric views of an embodiment of implant 100. Specifically, FIG. 3 is a posterior isometric view while FIG. 4 is an anterior isometric view. In FIGS. 3-4, implant 100 is understood to be configured with an anterior side 110 and a posterior side 112. Implant 100 may also include a first lateral side 114 and a second lateral side 116 that extend between posterior side 112 and anterior side 110 on opposing sides of implant 100. Furthermore, implant 100 may also include a superior side 130 and an inferior side 140.

Implant 100 may also be associated with various edges that are located at the intersections between various sides. For example, superior side 130 and first lateral side 114 may meet at a superior-lateral edge. Likewise, inferior side 140 and first lateral side 114 may meet at an inferior-lateral edge. It may be appreciated that the term "edge" as used herein is not limited to a precise contour of implant 100 and is used instead to refer to a general region proximate the intersection of two sides or faces of implant 100.

Reference is also made to directions or axes that are relative to the implant itself, rather than to its intended orientation with regards to the body. For example, the term "central" refers to a part that is located closer to the center of the implant. As used herein, the "center of the implant" is generally defined as a vertical axis extending through the approximate middle of the implant, which may be approximately the location of the center of mass or the dimensional middle (i.e., equidistant from opposing sides.

An implant may also be associated with various axes. Referring to FIG. 3, implant 100 may be associated with a lateral axis 111 that extends along implant 100 between first lateral side 114 and second lateral side 116. Additionally, implant 100 may be associated with a posterior-anterior axis 113 that extends between posterior side 112 and anterior side 110. Moreover, implant 100 may be associated with a vertical axis 115 (which may also be referred to as a superior-inferior axis) that extends along the thickness dimension of implant 100 and which is generally perpendicular to both lateral axis 111 and posterior-anterior axis 113.

An implant may also be associated with various reference planes or surfaces. As used herein, the term "median plane" refers to a vertical plane that passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the transverse plane.

Implant 100 is comprised of one or more body members attached to one or more bone contacting elements. In the embodiments shown in FIGS. 3-4, implant 100 includes a first body member 120. Body member 120 generally comprises a block-like member forming a solid end or side for implant 100.

Some embodiments can include one or more fastener-receiving provisions. In some embodiments, an implant can include one or more threaded cavities. In some embodiments, a threaded cavity can be configured to mate with a corresponding threaded tip on an implantation tool or device. In other embodiments, a threaded cavity can receive a fastener for purposes of fastening an implant to another device or component in an implantation system that uses multiple implants and/or multiple components.

As best seen in FIG. 4, implant 100 includes a threaded cavity 170 disposed in first body member 120. In some embodiments, threaded cavity 170 may receive the threaded tip of an implantation tool (not shown). Such a tool could be used to drive implant 100 between adjacent vertebral bodies. In some embodiments, first body member 120 may include one or more screw plates 530. Screw plates 530 may include components configured to assist insertion and placement of implant 100 within a patient. In this embodiment, the outer surface of screw plates 530 is substantially planar with the remaining perimeter surface of body 502 (see FIG. 5). In other embodiments, portions of screw plates 530 can extend beyond perimeter surface 535 of body 502 of implant 100.

In the exemplary embodiment, first body member 120 and screw plates 530 are disposed at an anterior end of implant 100. This configuration facilitates an ALIF approach to implantation of implant 100. Alternatively, in other embodiments, implant 100 could comprise one or more body members and/or screw plates on first lateral side 114, on second lateral side 116, and/or at an oblique angle in order to facilitate implantation from a non-ALIF approach.

In some embodiments, variations in height or vertical thickness between anterior side 110 and posterior side 112 may allow for an implant with hyper-lordotic angles between the inferior and superior surfaces. In other embodiments, variations in vertical thickness may be used to control the relative rigidity of the device in different locations. In other embodiments, implant 100 may have similar heights at anterior side 110 and posterior side 112.

In some embodiments, implant 100 may include one or more bone contacting elements or struts 160 that may be attached, and/or continuously formed with one another. As used herein, each bone contacting element comprises a distinctive member or element that spans a region or area of an implant. In some embodiments, these elements may overlap or intersect, similar to elements in a lattice or other 3D mesh structure. In other embodiments, the elements may not overlap or intersect. Some embodiments may use elongated elements, in which the length of the element is greater than its width and its thickness. For example, in embodiments where an element has an approximately circular cross-sectional shape, the element has a length greater than its diameter. In the embodiments seen in FIGS. 3-4, each bone contacting element is seen to have an approximately rounded or circular cross-sectional shape (i.e., the element has the geometry of a solid tube) along at least a portion of the element. However, in other embodiments, an element could have any other cross-sectional shape, including, but not limited to, various polygonal cross-sectional shapes (e.g., triangular, rectangular, etc.), as well as any other regular and/or irregular cross-sectional shapes. Examples of embodiments including a bone contacting element with a flattened cross-sectional shape are shown in FIGS. 14-19 and discussed in further detail below. In some cases, the cross-sectional shape of a bone contacting element could vary along its length (e.g., the diameter could change along its length).

Geometry of Bone Contacting Elements

Embodiments can include provisions for protecting bone growth along and adjacent to bone contacting elements of an implant. In some embodiments, a bone contacting element can be configured with a geometry that helps to protect new bone growth in selected regions that may be referred to as "protected fusion zones." In a protected fusion zone, new bone growth may be partially protected from forces transmitted directly between vertebrae and bone contacting surfaces of an implant, thereby increasing the rate at which new bone growth may propagate through the implant.

In some embodiments, a bone contacting element can have a spiral, helical or twisted geometry that provide a series of such protected fusion zones for enhanced bone growth. In other embodiments, a bone contacting element can have a planar undulating geometry (e.g., sinusoidal) that may also create protected fusion zones. In some embodiments, an implant may include bone contacting elements with a helical geometry and other bone contacting elements with a sinusoidal or planar undulating geometry.

Some bone contacting elements may have a generalized helical geometry. As used herein, a "generalized helical geometry" or "spiraling geometry" refers to a geometry where a part (portion, member, etc.) winds, turns, twists, rotates, or is otherwise curved around a fixed path. In some cases, the fixed path could be straight. In other cases, the fixed path can be curved. In the present embodiments, for example, the fixed path is generally a combination of straight segments and curved segments.

Curves having a generalized helical geometry (also referred to as generalized helical curves) may be characterized by "coils", "turns," or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Generalized helical curves need not be circular or even round. In some embodiments, for example, a generalized helical curve could have a linearly segmented shape (or locally polygonal shape) such that each "coil" or "turn" is comprised of straight line segments rather than arcs or other curved segments. Generalized helical curves may also include combinations of curved and straight segments.

For purposes of characterizing the geometry of helical bone contacting elements, each bone contacting element can be identified with one or more curves. Each bone contacting element may be identified with a central curve. The central curve of each bone contacting element may be defined as a curve that extends along the length (or longest dimension) of the bone contacting element such that each point along the curve is centrally positioned within the bone contacting element. In addition, each bone contacting element may be identified with one or more exterior surface curves. An exterior surface curve of a bone contacting element may be defined as a curve that extends along the length (or longest dimension) of the bone contacting element such that each point along the curve is positioned on the exterior surface.

In some cases, bone graft material may be used with the disclosed implants. For purposes of this disclosure and claims, the term "bone graft material" shall include any type of bone graft material, including harvested bone graft material and/or bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft as a bone graft material. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products that combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone graft materials.

Figure 5:
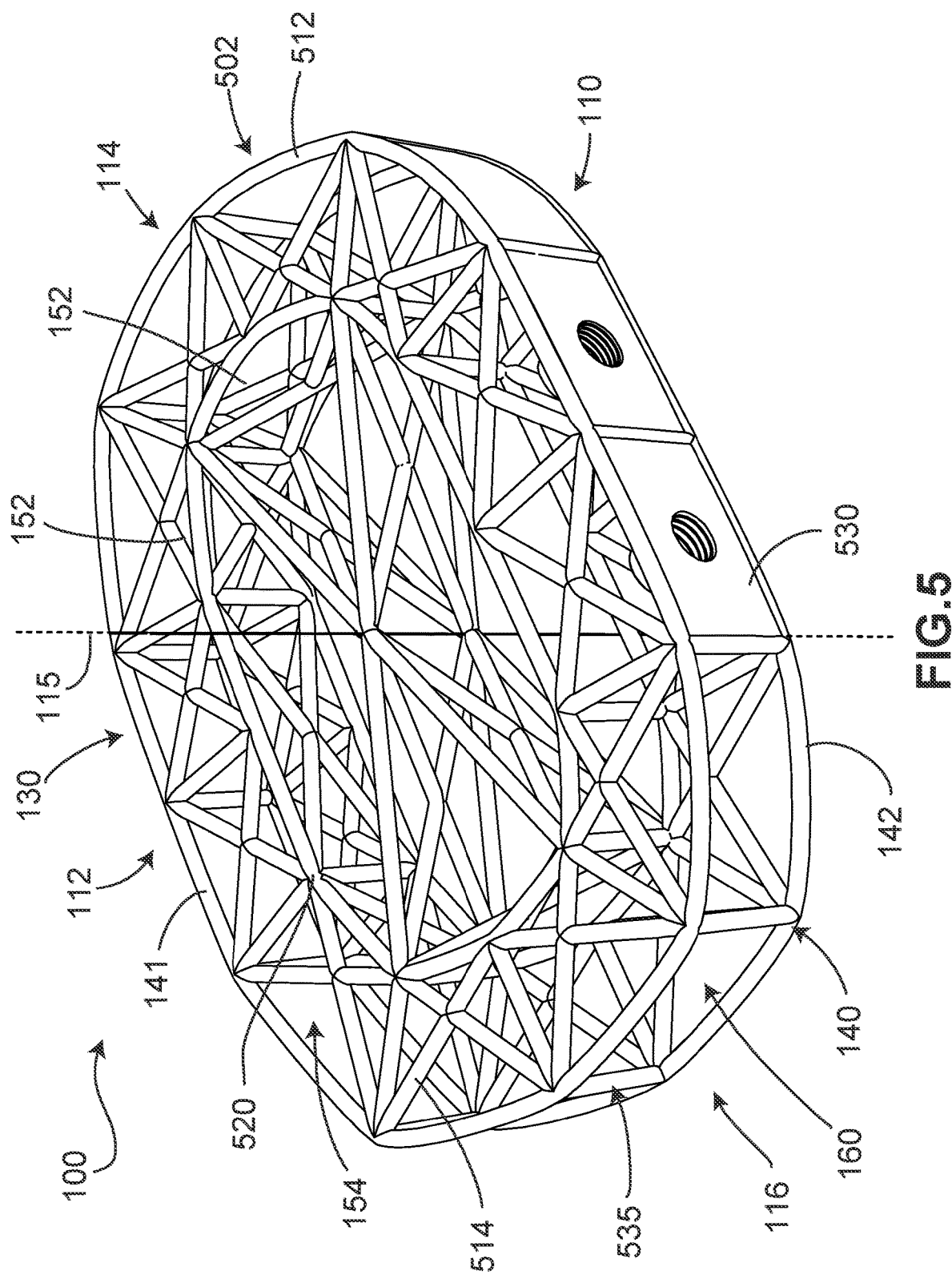
FIG. 5 is a schematic isometric view of an embodiment of an implant configured for improved flow of bone graft material into the implant.

FIG. 5 is a schematic isometric view of an embodiment of implant 100 configured for improved flow of bone graft material into the implant. As shown in FIG. 5, implant may include body 502 formed as an open truss structure. For example, body 502 may be formed as an open lattice structure made of a plurality of bone contacting elements or struts 160.

As also shown in FIG. 5, body 502 may have opposing end surfaces, including a superior surface 141 on superior side 130 and an inferior surface 142 on inferior side 140. Superior surface 141 may present a bone confronting surface configured to contact a vertebra above the implant when implanted. Inferior surface 140 may present a bone confronting surface configured to contact a vertebra below the implant when implanted. As shown in FIG. 5, implant 100 may include a perimeter surface 535, the perimeter surface extending around an outer periphery of body 502.

In addition, as also shown in FIG. 5, in some embodiments, body 502 may have a generally annular shape. For example, in some embodiments, body 502 may include a central portion 152 and a peripheral portion 154 extending inward from perimeter surface 535 toward central portion 152. Central portion 152 is disposed approximately within the middle or center of body 502 of implant 100. Central portion 152 may have a central axis oriented substantially vertically. In some embodiments, the central axis of central portion 152 may coincide with vertical axis 115, as shown in FIG. 5. Peripheral portion 154 is disposed outward from central portion 152 and generally surrounds central portion 152.

A number of factors may influence the ease and extent to which bone graft material may flow into the spaces within the truss structure of the implant. For example, the viscosity and composition of the bone graft material can affect the introduction of bone graft material into the implant. Higher viscosity of the bone graft material and larger solid pieces of bone and bone substitute may reduce the ease with which bone graft material may flow generally. In addition, the density of the truss structure affects the size of the openings through which the bone graft material must flow, and thus, can influence the flow of material into the implant.

In some embodiments, the implant may include provisions to facilitate the introduction of bone graft material into the implant between the struts. For example, in some embodiments, the density of struts and/or trusses may differ in different portions of the implant. In some cases, the central portion may have a lower density of struts than the peripheral portion. In such embodiments, the higher density of struts in the peripheral portion may provide load bearing support around the periphery of adjacent vertebrae, which is typically a more structurally robust type of bone, like cortical bone. The lower density of struts in the central portion may facilitate the introduction of bone graft material, which promotes fusion of the adjacent vertebrae between which the implant is inserted.

As shown in in FIG. 5, peripheral portion 154 may include a first set of trusses, the first set of trusses having a first density of trusses. Central portion 152 may include a second set of trusses, the second set of trusses having a second density of trusses. In some embodiments, the first density of trusses in peripheral portion 154 may be greater than the second density of trusses in central portion 152, as shown in FIG. 5.

Struts 160 forming the open lattice structure of body 502 of implant 100 are generally elongate members having a longitudinal length and a lateral width, with the longitudinal length being longer than the lateral width. Struts 160 can include one or more outer struts 512 and one or more inner struts 514. In this embodiment, outer struts 512 are disposed along the perimeter edge of implant 100 and define the boundary of peripheral portion 154. Outer struts 512 can include substantially straight segments and/or curved or arched segments. In some embodiments, outer struts 512 may include combinations of curved and straight segments that assist with providing and defining the overall shape of implant 100.

Inner struts 514 extend from the perimeter edge of implant 100 defined by outer struts 512 inward toward central portion 152 of body 502. Inner struts 514 intersect with one another at one or more nodes 520. A plurality of inner struts 514 intersects at a plurality of nodes 520 to collectively form the open lattice structure of body 502. In this embodiment, inner struts 514 are substantially straight segments. In other embodiments, inner struts 514 can include substantially straight segments, curved or arched segments, and/or a combination of curved and straight segments to form an open lattice structure.

Figure 6:
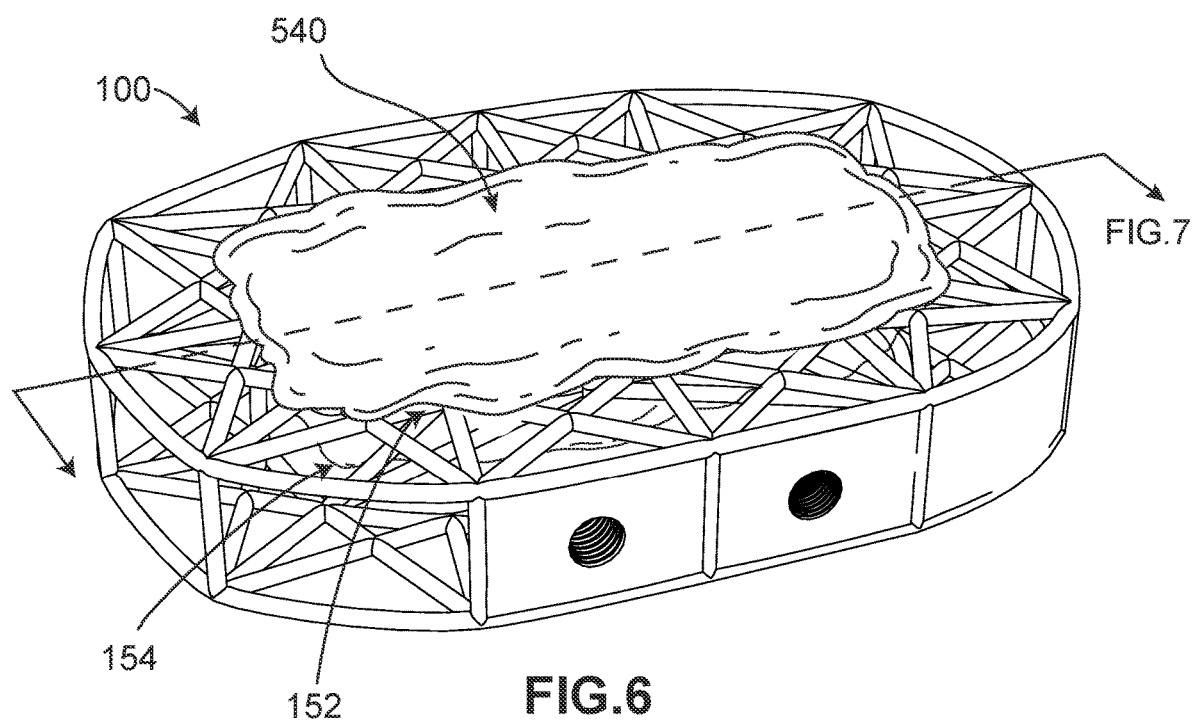
FIG. 6 is a schematic top perspective view of the implant of FIG. 5 with bone graft material being added to the central portion of the implant.
Figure 7:
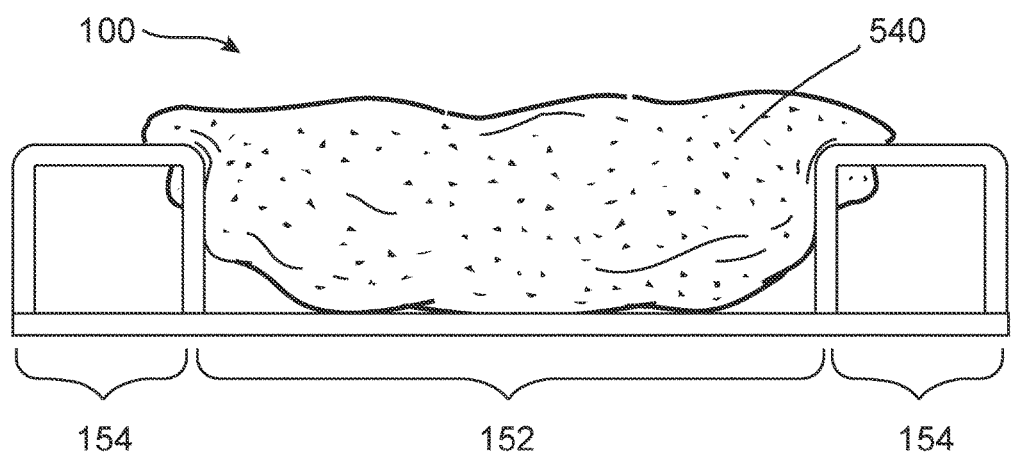
FIG. 7 is a schematic cross-sectional view of the implant of FIG. 5 with bone graft material being added to the central portion of the implant viewed from the perspective indicated in FIG. 6.

FIGS. 6 and 7 illustrate the addition of bone graft material to the implant. As shown in FIGS. 6 and 7, prior to implantation, bone graft material may be introduced into the inner region of the implant between the struts. For example, FIG. 6 shows bone graft material 540 being added to central portion 152 of implant 100. FIG. 7 shows a cross-sectional view of implant 100 with bone graft material 540 being introduced to central portion 152 of implant 100. As discussed above, in some embodiments, the second set of trusses formed in the central portion 152 of implant 100 may be arranged to facilitate the flow of bone graft material, for example, by having a lower density than the first set of trusses formed in the peripheral portion 154 of implant 100. Accordingly, bone graft material 540 may flow into the inner region of implant 100 more readily through the superior surface of implant 100 in central portion 152 than it does through peripheral portion 154.

In some embodiments, the implant may include provisions to facilitate spread of bone graft material from the central portion radially outward into the peripheral portion of the implant. For example, in some embodiments, the implant may include an interface portion between the central portion and the peripheral portion. For example, the interface portion may be a boundary of truss units defining a boundary between the central portion and the peripheral portion. Each of these truss units may be arranged in a generally vertical orientation in a substantially vertical plane. Truss units forming the perimeter surface of the implant may also be arranged in a substantially vertical plane. Thus, the truss units of the interface portion may be arranged in planes that are substantially parallel to planes in which the truss units of the perimeter surface are arranged. In order to facilitate spread of bone graft material from the central portion through the truss units of the interface portion into the peripheral portion, the density of struts in the interface portion may be less than the density of struts in the perimeter surface. For example, in some embodiments, the density of truss units in the interface portion may be less than the density of truss units in the perimeter surface.

Figure 8:
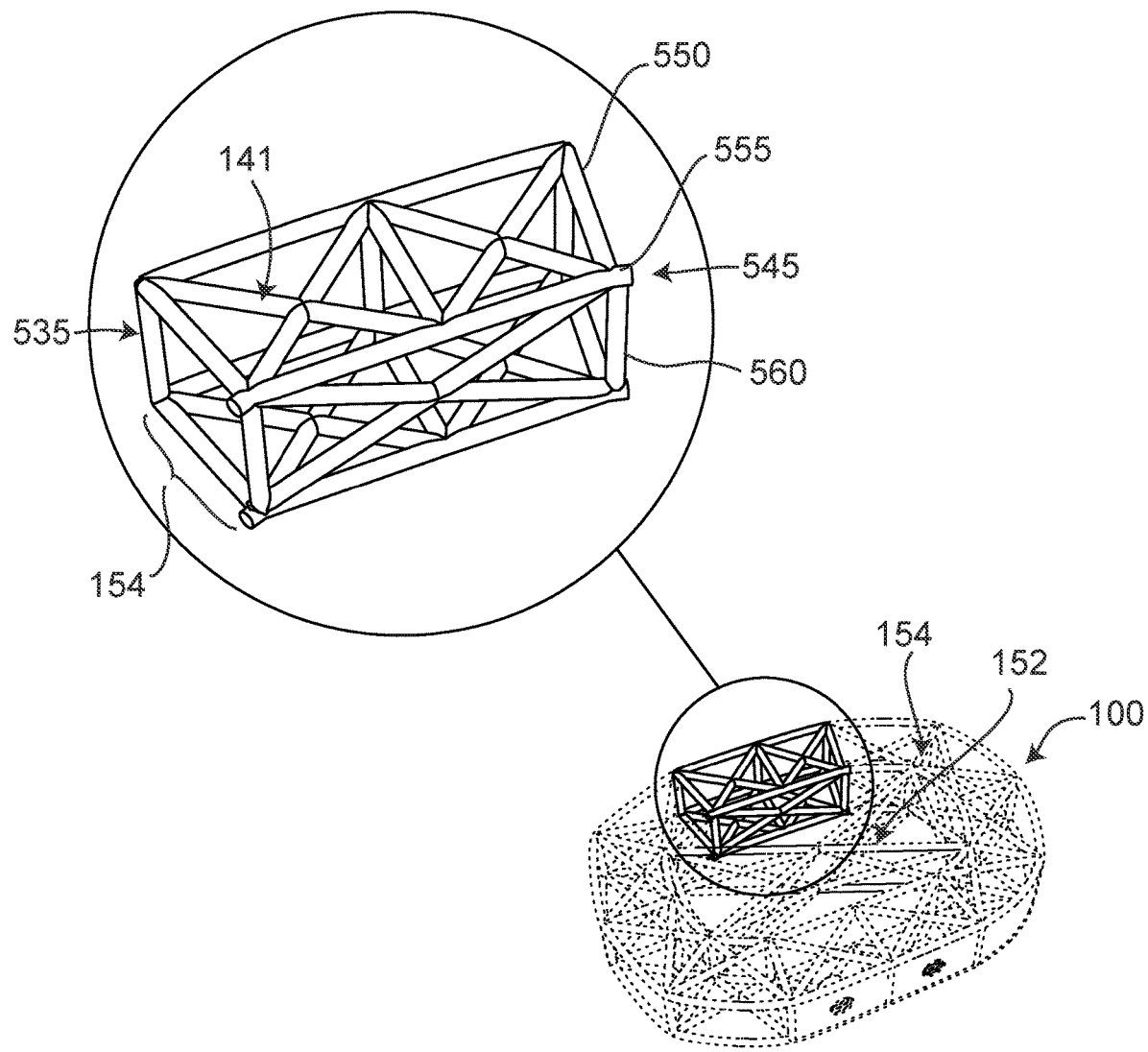
FIG. 8 is a schematic perspective view of the implant of FIG. 5 with an area of the implant enlarged for clarity.

FIG. 8 is a schematic perspective view of implant 100 with an area of implant 100 enlarged for clarity. As shown in FIG. 8, peripheral portion 154 meets central portion 152 at an interface portion 545. For example, peripheral portion 154 and central portion 152 may share common nodes in interface portion 545. As further shown in FIG. 5, a plurality of struts of the second set of trusses may connect to a plurality of nodes of the first set of trusses. For example, the first set of trusses includes a first strut 550 and a first node 555. In addition, the second set of trusses includes a second strut 560. As shown in FIG. 8, first node 555 connects first strut 550 with second strut 560.

Figure 9:
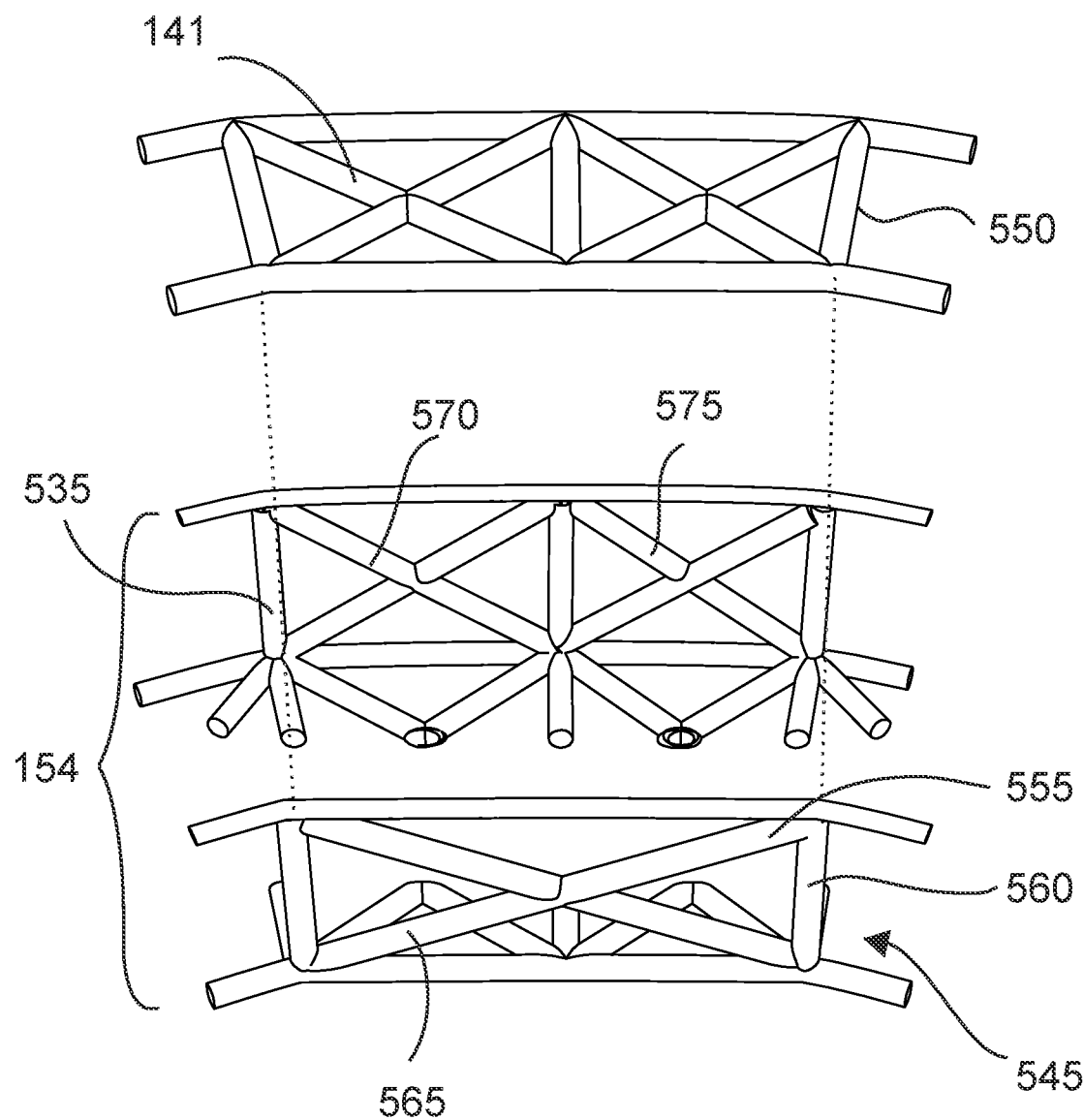
FIG. 9 is a schematic partial exploded view of the area of the implant enlarged in FIG. 8, showing the truss structure of a superior surface lifted off the peripheral portion of the implant.

FIG. 9 is a schematic partial exploded view of the area of the implant enlarged in FIG. 8. FIG. 9 shows the truss structure of superior surface 141 lifted off peripheral portion 154 of implant 100. In some embodiments, the density of truss units in interface portion 545 may be less than the density of truss units in perimeter surface 535. For example, as shown in FIG. 9, interface portion 545 may include a first interface truss unit 565, shown in dashed lines. Perimeter surface 535 may include a first peripheral truss unit 570 and a second peripheral truss unit 575. As shown in FIG. 9, first interface truss unit 565 corresponds radially with the combination of first peripheral truss unit 570 and second peripheral truss unit 575 (see also FIG. 8).

Figure 10:
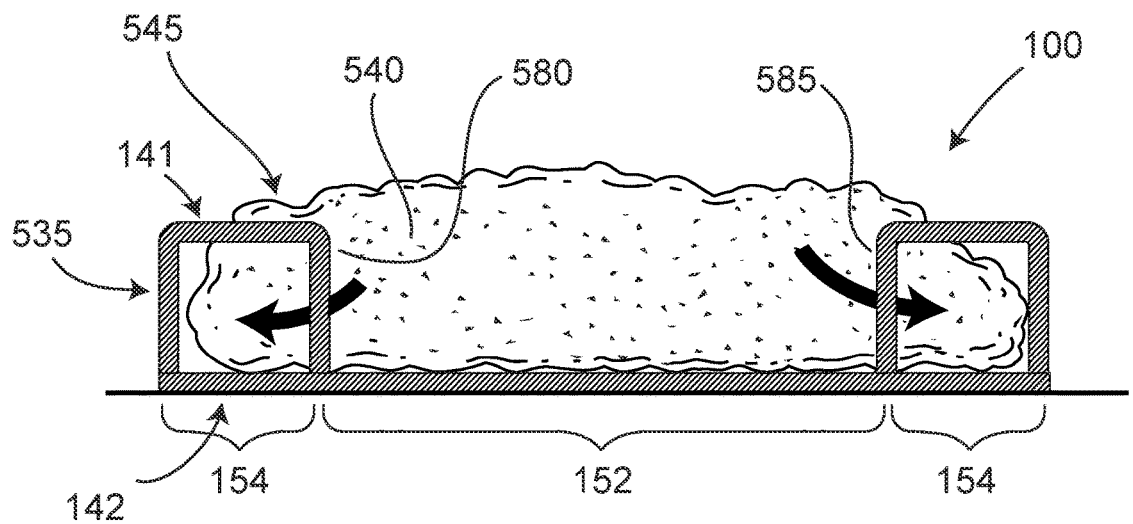
FIG. 10 is a schematic cross-sectional view of an implant with the bone graft material introduced from the central portion of the implant into the peripheral portion.

FIG. 10 is a schematic cross-sectional view of implant 100 with bone graft material 540 introduced from central portion 152 of implant 100 into peripheral portion 154. As shown in FIG. 10, bone graft material 540 may flow from central portion 152 across interface portion 545 into peripheral portion 154. That is, bone graft material 540 may flow around the struts of interface portion 545, such as a first interface strut 580 and a second interface strut 585.

Figure 11:
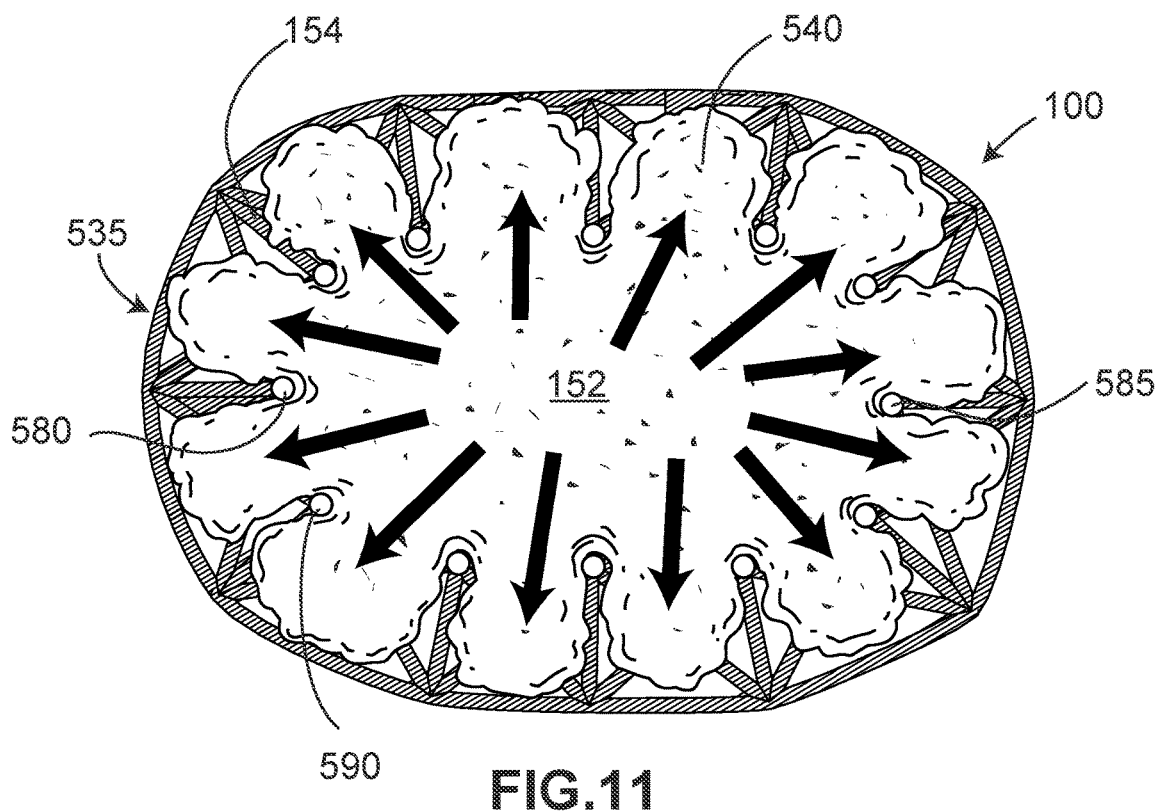
FIG. 11 is a schematic cutaway top view of an implant with the truss structure of the superior surface removed and bone graft material introduced from the central portion of the implant into the peripheral portion as shown in FIG. 10.

FIG. 11 is a schematic cutaway top view of implant 100 with the truss structure of the superior surface removed and bone graft material 540 introduced from the central portion of the implant into the peripheral portion as shown in FIG. 10. FIG. 11 shows bone graft material 540 flowing around the struts of the interface portion, such as first interface strut 580, second interface strut 585, and a third interface strut 590. Although implant 100 may include interface struts having a variety of angular orientations, for purposes of clarity, only interface struts having substantially vertical orientations are shown in FIG. 11.

FIG. 12 shows an enlarged view of a portion of FIG. 11, showing a cutaway top view of implant 100 with the truss structure the superior surface removed and bone graft material 540 introduced from central portion 152 of implant 100 into peripheral portion 154 around interface struts, such as third interface strut 590. FIG. 13 is an enlarged schematic cutaway top view of a single strut area of the implant in FIG. 12. In particular, FIG. 13 shows a cross-sectional view of third interface strut 590 and bone graft material 540 flowing around it. As shown in FIG. 13, third interface strut 590 may have a substantially circular cross-sectional shape.

As further shown in FIG. 13, the width (i.e., diameter) of third interface strut 590 may obstruct the flow of bone graft material 540. The spacing between portions of bone graft material 540 is illustrated by an initial gap 610 before they converge. It will be noted that the size of initial gap 610 may generally correspond to the width (i.e., diameter) 591 of third interface strut 590.

In some cases, the implant may include provisions to facilitate the flow of bone graft material past the struts, such as the interface struts. For example, in some embodiments, the struts may be provided with a non-circular cross-sectional shape. In some embodiments, the struts may have an oblong cross-sectional shape. By having an oblong cross-sectional shape, the width of the strut may be made reduced in one direction while still maintaining the same cross-sectional area. The reduced width of the strut may enable more flow of bone graft material past the strut. Further, the bone graft material may converge behind the strut more readily after flowing past it, thus filling the volume behind the strut more completely. In some embodiments, the struts may not only be oblong, but may also include further provisions to facilitate convergence of the bone graft material behind the strut. For example, in some embodiments, the struts may have a substantially airfoil cross-sectional shape. The airfoil cross-sectional shape may provide the struts with a narrower width to reduce the obstruction to flow by increasing the size of the passages between struts, as well as a tapered profile to facilitate convergence of the bone graft material behind the strut as the bone graft material flows past the struts.

FIG. 14 is an enlarged schematic cutaway top view of a single strut area of an implant wherein the strut has an oblong cross-sectional shape. As shown in FIG. 14, a fourth interface strut 595 may have a substantially oblong cross-sectional shape. As further shown in FIG. 14, fourth interface strut 595 may have a width that is slightly smaller than third interface strut 590. Accordingly, when flowing around fourth interface strut 595, the portions of bone graft material 540 that separate around fourth interface strut 595 may have an initial gap 615 behind the strut before they converge. It will be noted that the size of initial gap 615 may generally correspond to width 596 of fourth interface strut 595. Since width 596 of fourth interface strut 595 is slightly smaller than width 591 of third interface strut 590, the size of initial gap 615 may be slightly smaller than initial gap 610 formed in bone graft material 540 behind third interface strut 590, shown in FIG. 13. Thus, the oblong cross-sectional shape of fourth interface strut 595 may facilitate flow of bone graft material 540.

Figure 15:
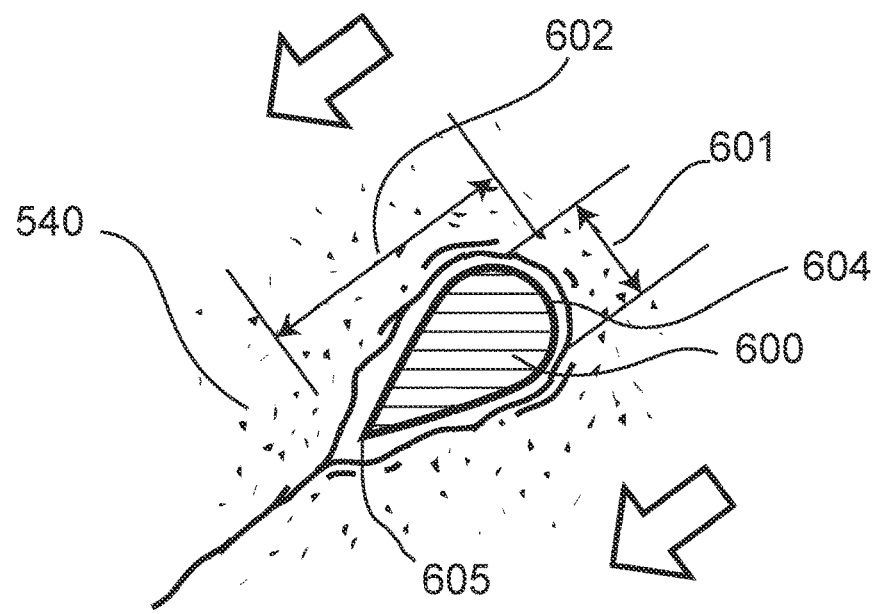
FIG. 15 is an enlarged schematic top view of an area of a single strut of an implant wherein the strut has an airfoil cross-sectional shape.

FIG. 15 is an enlarged schematic top view of a single strut area of an implant wherein the strut has an airfoil cross-sectional shape. As shown in FIG. 15, a fifth interface strut 600 may have an airfoil cross-sectional shape. That is, fifth interface strut 600 may have a cross-sectional shape having a rounded leading edge 604 and a tapered trailing edge 605. As illustrated in FIG. 15, fifth interface strut 600 may have a cross-sectional width 601 and a cross-sectional length 602, wherein cross-sectional length 602 is longer than cross-sectional width 601. However, unlike the circular and oblong cross-sectional shapes shown in FIGS. 13 and 14, the airfoil cross-sectional shape shown in FIG. 15 may create substantially no gap behind the strut due to the tapered configuration of the strut. For example, when using a round or oblong strut, the bone graft material may separate and converge over a distance behind the strut (as shown in FIGS. 13 and 14). In contrast, the tapered trailing portion of the airfoil may occupy the volume of space in which the gap would otherwise be formed behind the strut. This may facilitate the flow of bone graft material and the filling of the internal volume of the implant with bone graft material.

Figure 16:
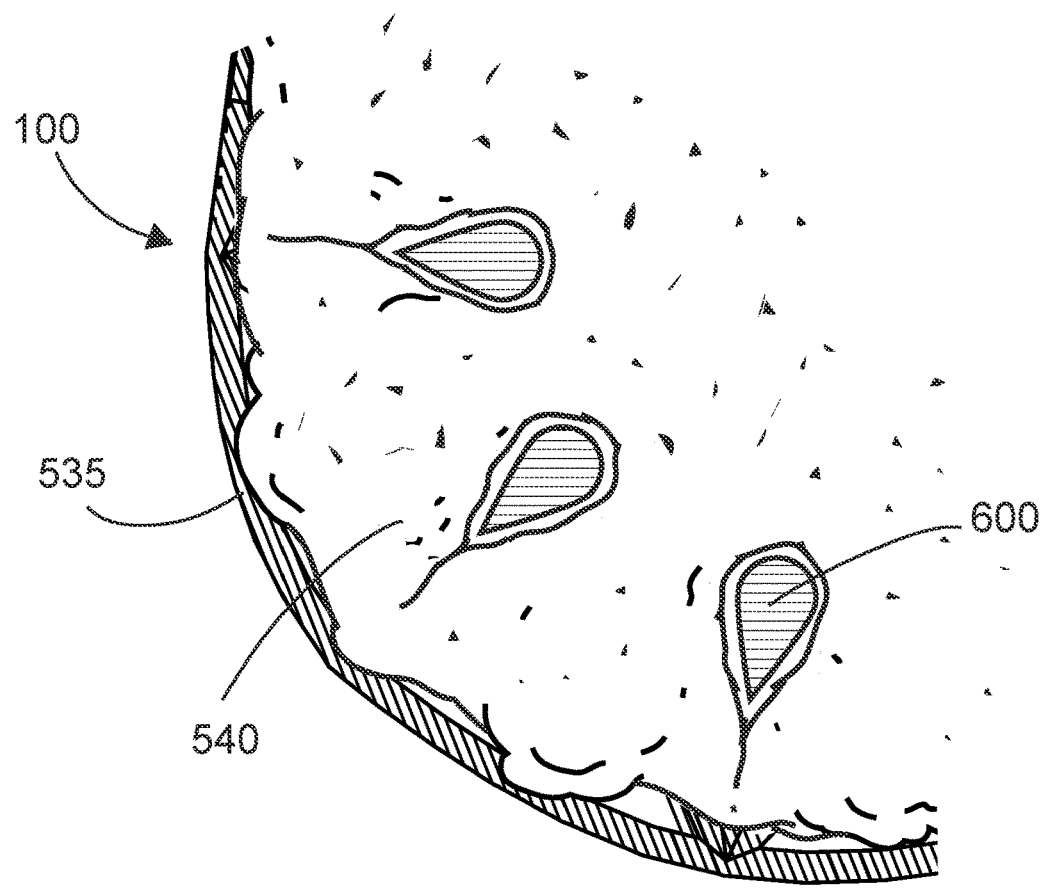
FIG. 16 is a schematic cutaway partial top view of an implant with the truss structure of the superior surface removed and bone graft material introduced from the central portion of the implant into the peripheral portion wherein the strut has an airfoil cross-sectional shape.

FIG. 16 illustrates a larger portion of an implant, showing multiple airfoil-shaped interface struts, including fifth interface strut 600. As shown in FIG. 16, there may be very little space, if any, behind the airfoil struts that is not filled with bone graft material 540. As also shown in FIG. 16, in some embodiments, multiple struts having non-circular cross-sectional shapes may cooperate to direct bone graft material into a desired area of the implant. For example, two or more non-circular struts may direct bone graft material into a predetermined region of the peripheral portion of the implant.

The airfoil shape illustrated in the accompanying drawings is intended to be relatively generic. Struts may have any of a number of different airfoil cross-sectional shapes. Exemplary airfoils may be concave, convex, or may simply have a trailing portion with a consistent taper. In some cases, the sides of the airfoil may be shaped differently in order to direct the flow of bone graft material in a particular direction. The airfoils may also be oriented in a variety of directions. In some cases, the long axis of the airfoil may be oriented substantially radially with respect to the central axis of the implant, and thus, in the direction of flow of bone graft material. In other cases, one or more airfoil-shaped struts may be oriented with the cross-sectional length oriented at a non-zero angle with respect to the direction of flow. Non-zero angle orientations may be implemented to redirect flow of bone graft material to particular portions of the implant's inner volume. For example, in some embodiments, the cross-sectional length of the struts may be oriented at an angle with respect to the radial direction of the implant. In such embodiments, when bone graft material is introduced into the central portion of the implant and flows radially outward, the non-circular struts oriented at non-zero angles may redirect the radial flow into predetermined regions of the implant. In some embodiments, the interface struts may have different shapes and orientations from one another.

The longitudinal length of non-circular struts may be oriented at non-zero angles with respect to horizontal. For example, in some embodiments, not only vertically oriented struts, but also diagonally oriented interface struts may have non-circular cross-sectional shapes. Also, non-circular struts may be inclined along the cross-sectional length. In addition, it will be noted that other struts of the disclosed implant besides the interface struts between the central portion and the peripheral portion of the implant may have oblong or airfoil cross-sectional shapes. For example, in some embodiments, struts forming the superior surface of the central portion of the implant may have an oblong or airfoil cross-sectional shape with a cross-sectional length oriented substantially vertically. Such struts would facilitate the introduction of bone graft material into the central portion of the implant. In some embodiments, the struts forming the superior surface of the central portion of the implant may have non-circular cross-sectional shapes with their cross-sectional lengths oriented non-vertically in order to direct the flow of bone graft material to desired areas of the internal volume of the implant.

Figure 17:
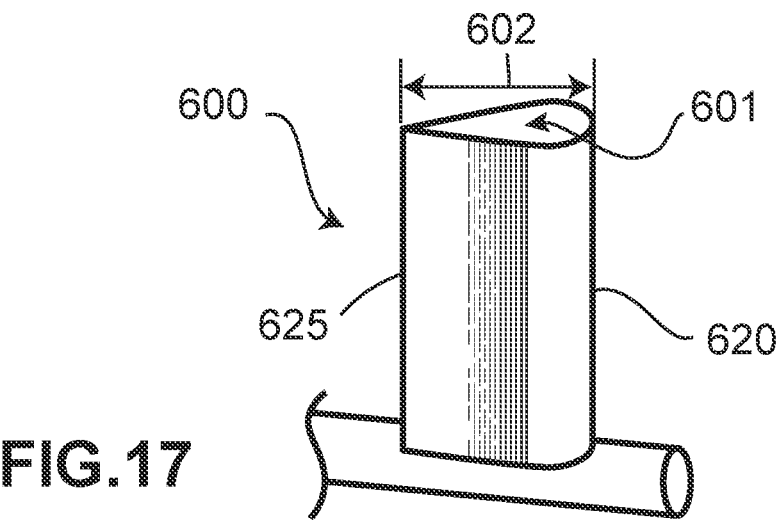
FIG. 17 is a schematic perspective view of a vertically oriented strut having an airfoil cross-sectional shape.

FIG. 17 is a schematic perspective view of a vertically oriented strut having an airfoil cross-sectional shape. As shown in FIG. 17, fifth interface strut 600 may have an airfoil cross-sectional shape. For example, fifth interface strut 600 may have a substantially rounded leading edge 620, a tapered body, and a trailing edge 625. FIG. 17 also shows cross-sectional width 601 and cross-sectional length 602 of fifth interface strut 600.

Figure 18:
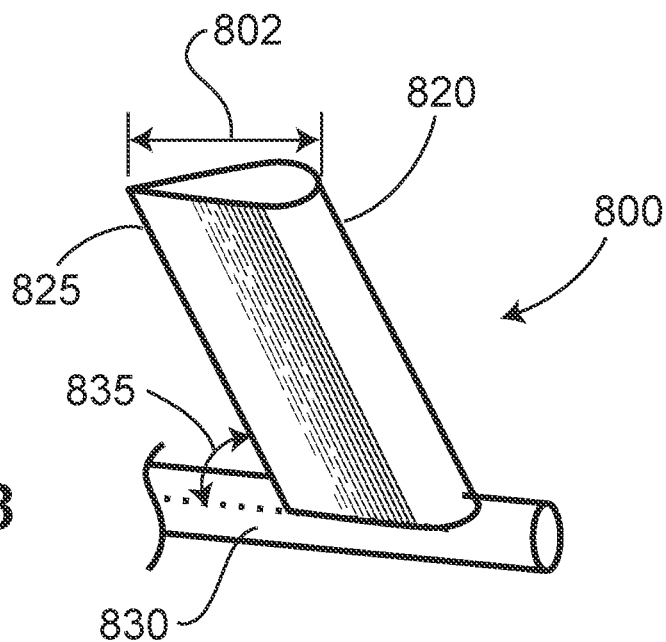
FIG. 18 is a schematic perspective view of a strut having an airfoil cross-sectional shape oriented with an acute trailing edge angle with respect to a horizontal base.

In some embodiments, non-circular struts may be inclined along the cross-sectional length. For example, FIG. 18 is a schematic perspective view of a strut having an airfoil cross-sectional shape oriented with an acute trailing edge angle with respect to a horizontal base. As shown in FIG. 18, a strut 800 may have a leading edge 820 and a trailing edge 825. For purposes of reference, strut 800 is shown as being attached to a base strut 830. Base strut 830 may have any suitable orientation, but is included in FIG. 18 to illustrate a horizontal reference. As shown in FIG. 18, strut 800 may be inclined in the direction of its cross-sectional length 802. For example, strut 800 may have an acute trailing edge angle 835 between horizontal base strut 830 and trailing edge 825.

Figure 19:
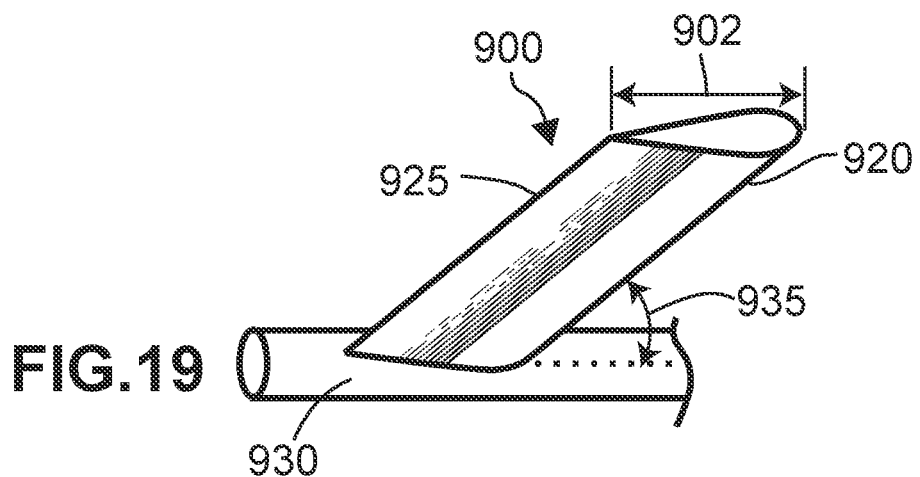
FIG. 19 is a schematic perspective view of a strut having an airfoil cross-sectional shape oriented with an acute leading-edge angle with respect to a horizontal base.

FIG. 19 is a schematic perspective view of a strut having an airfoil cross-sectional shape oriented with an acute leading-edge angle with respect to a horizontal base. As shown in FIG. 19, a strut 900 may have a leading edge 920 and a trailing edge 925. For purposes of reference, strut 900 is shown as being attached to a base strut 930. Base strut 930 may have any suitable orientation, but is included in FIG. 19 to illustrate a horizontal reference. As shown in FIG. 19, strut 900 may be inclined in the direction of its cross-sectional length 902. For example, strut 900 may have an acute leading edge angle 935 between horizontal base strut 930 and leading edge 920.

Struts having different orientations and/or cross-sectional shapes may be used in any suitable areas of the implant in order to provide the desired characteristics, such as strength, rigidity, flow of bone graft material, bone attachment, and other performance characteristics. In some embodiments, non-circular struts having different cross-sectional shapes and/or orientations as described above may be used within the same implant in different areas.

Figure 20:
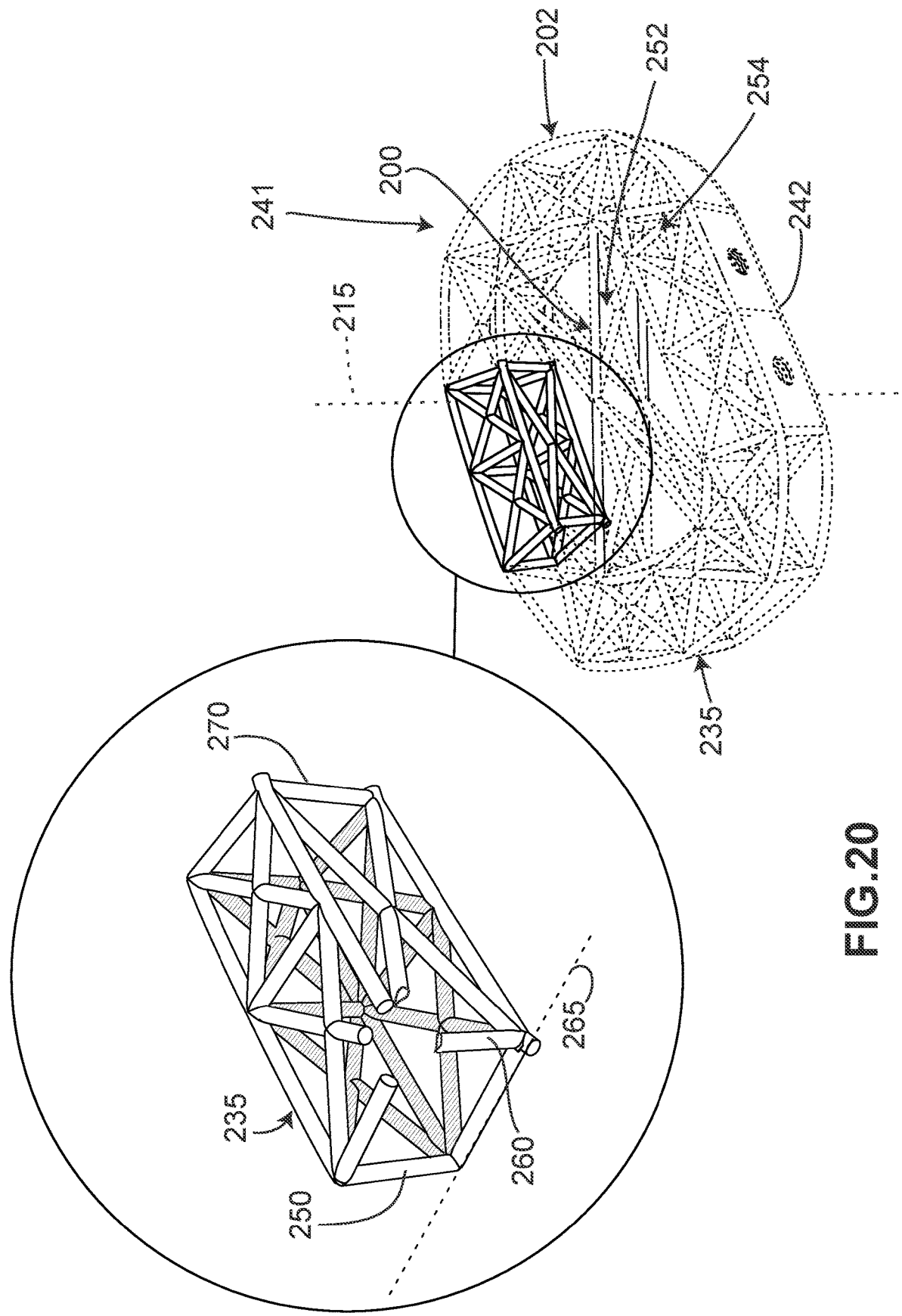
FIG. 20 is a schematic perspective view of an implant with an enlarged cutaway view of certain struts.

FIG. 20 illustrates an exemplary embodiment including an airfoil-shaped interface strut. As shown in FIG. 20, an implant 200 may include a body 202 having an open truss structure. Body 202 may have a generally annular shape with opposing end surfaces, the opposing end surfaces including a superior surface 241 and an inferior surface 242. Body 202 may also have a perimeter surface 235 extending around an outer periphery of body 202. Body 202 may also have a central portion 252 and a peripheral portion 254, with peripheral portion 254 extending inward from perimeter surface 235 toward central portion 252. As shown in FIG. 20, central portion 252 may have a central axis 215.

Body 202 may include a first strut 250 disposed on perimeter surface 235. Body 202 may also include a second strut 260 disposed inward of perimeter surface 235 so that second strut 260 is closer to central axis 215 than first strut 250. Central axis 215 and second strut 260 define a radial direction that extends from central axis 215 to second strut 260 as indicated by a radial axis 265 in FIG. 20.

As shown in FIG. 20, second strut 260 may have a non-circular cross-sectional shape with a cross-sectional length and a cross-sectional width, wherein the cross-sectional length is longer than the cross-sectional width. For example, as shown in FIG. 20, second strut 260 may have an airfoil cross-sectional shape. As further shown in FIG. 20, in some embodiments, the cross-sectional length of second strut 260 may extend along the radial direction identified by radial axis 265.

As also shown in FIG. 20, body 202 may include a third strut 270 disposed inward of perimeter surface 235. In some embodiments, third strut 270 may also have a non-circular cross-sectional shape. Accordingly, second strut 260 and third strut 270 may cooperate to direct bone graft material into a predetermined region of peripheral portion 254.

In some embodiments, second strut 260 and/or third strut 270 may be inclined with respect to first strut 250. For example, second strut 260 and/or third strut 270 may be oriented at a non-vertical angle (see, e.g., FIGS. 18 and 19).

The side profile of the implants shown in FIGS. 1-19 is intended to be generic in terms of the height of the implant. In some embodiments, the height of the implant may be substantially consistent across the entire implant. That is, the superior surface and the inferior surface may be substantially parallel. In other embodiments, the height may vary in different portions of the implant. For example, in some embodiments, the implant may be formed to have a posterior-anterior profile that promotes spinal lordosis. That is, the implant may have a lordotic angle. In addition, in some embodiments, the implant may have a convexity that promotes spinal lordosis.

Figure 21:
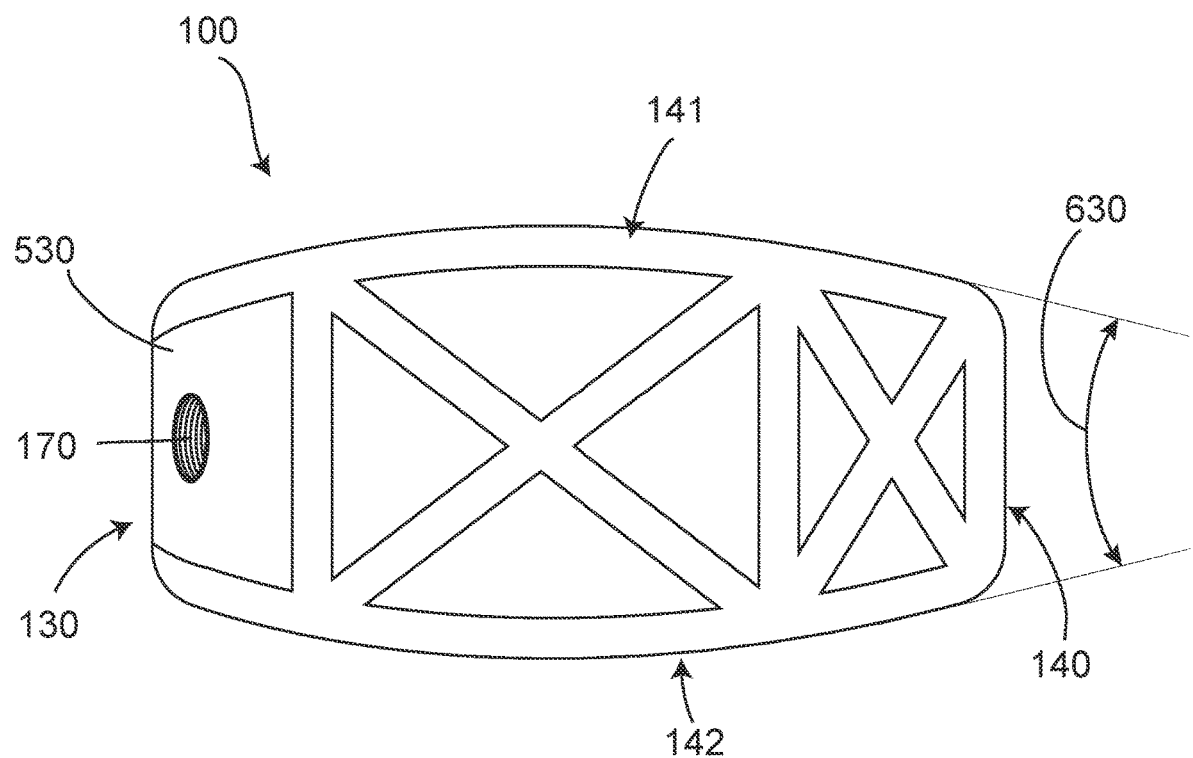
FIG. 21 is a schematic lateral view of an implant having a biconvex configuration.

FIG. 21 is a schematic lateral view of an implant 100 with an asymmetrical profile. FIG. 21 shows implant 100 as having a biconvex configuration. For example, as shown in FIG. 21, both superior surface 141 and inferior surface 142 may have convex configurations. In other embodiments, one or both of these surfaces may have a non-convex surface. For example, in some embodiments, one or both of superior surface 141 and inferior surface 142 may have substantially planar or convex surfaces. It will be noted that the truss structure shown in FIG. 21 is intended to be generic, with FIG. 21 being provided in order to illustrate the profile shape of implant 100.

In addition, as shown in FIG. 21, implant 100 may have a lordotic angle 630. Lordotic angle 630 may be any suitable angle. In some cases, lordotic angle 630 may be subtle, such as 5-10 degrees. In some cases, lordotic angle 630 may be moderate, such as approximately 10-25 degrees. In other cases, lordotic angle 630 may be a hyper-lordotic angle, which may be approximately 25-35 degrees.

ALTERNATIVE EMBODIMENTS

Figure 22:
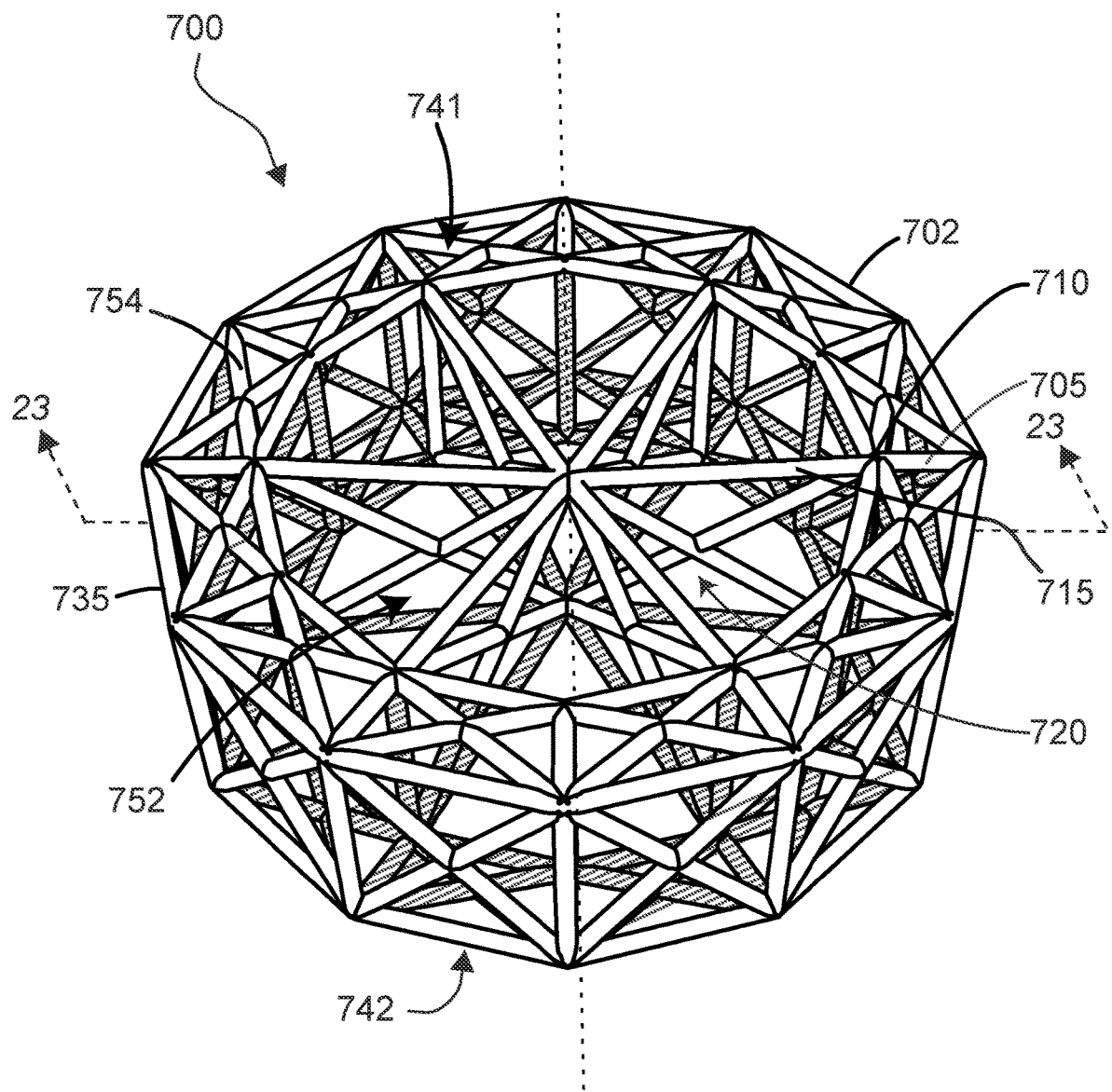
FIG. 22 is a schematic perspective view of an embodiment of an implant having an asymmetrical central truss structure.

FIG. 22 is a schematic perspective view of an embodiment of an implant having an asymmetrical central truss structure. As shown in FIG. 22, an exemplary intervertebral implant 700 may include a body 702 having an open truss structure. The body may have a generally annular shape with opposing end surfaces. The opposing end surfaces may include a superior surface 741 and an inferior surface 742. The body may also have a perimeter surface 735, perimeter surface 735 extending around an outer periphery of body 702. In addition, body 702 may have a central portion 752 and a peripheral portion 754, with peripheral portion 754 extending inward from perimeter surface 735 toward central portion 752.

Peripheral portion 754 may include a first set of trusses having a first density of trusses. Central portion 752 may include a second set of trusses having a second density of trusses. Similar to the embodiments discussed above, the first density of trusses in peripheral portion 754 may be greater than the second density of trusses in central portion 752. This may facilitate introduction of bone graft material into the inner volume of implant 700.

As shown in FIG. 22, the first set of trusses may include a first strut 705 and a first node 710. In addition, the second set of trusses may include a second strut 715. As shown in FIG. 22, first node 710 may connect first strut 705 with second strut 715. It will be appreciated that the length of first strut 705 defines a thickness of peripheral portion 754, and the length of second strut 715 defines a radial dimension of central portion 752. Thus, as shown in FIG. 22, in some embodiments, peripheral portion 754 may extend inward toward central portion 752 to achieve a substantially similar radial thickness around central portion 752 completely around the perimeter of the implant.

In some embodiments, peripheral portion 754 may be sized and configured to generally correspond to a region of denser bone, such as a cortical bone region of a confronting vertebral body. Accordingly, central portion 752 may be sized and configured to generally correspond to a region of bone that is less dense, such as a cancellous bone region of a confronting vertebral body.

In addition, in some embodiments, implant 700 may have an asymmetrical truss structure in central portion 752. For example, as shown in FIG. 22, central portion 752 may only include one layer of struts, such as second strut 715, which may define a portion of superior surface 741. As further shown in FIG. 22, the second set of trusses, may include a central hollow portion 720 configured to receive bone graft material.

Figure 23:
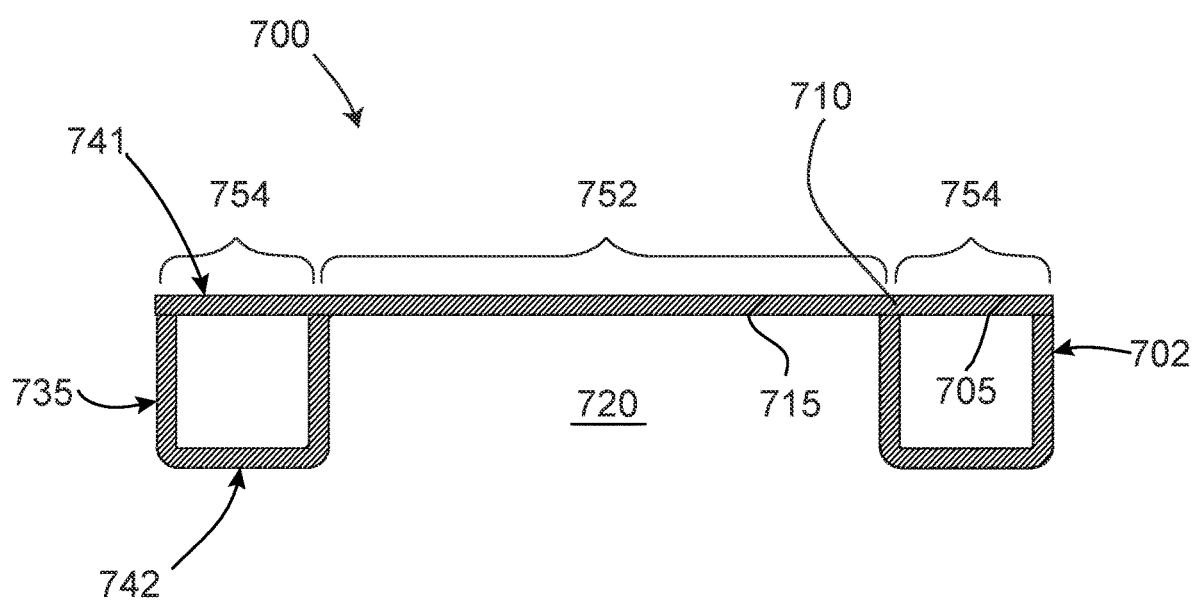
FIG. 23 is a schematic cross-sectional view of the implant shown in FIG. 22 illustrating a substantially conical hollow central portion.

FIG. 23 is a schematic cross-sectional view of implant 700. FIG. 23 further illustrates the thickness of peripheral portion 754. As also illustrated in FIG. 23, central hollow portion 720 may include a hollow base that is open to an end of body 702. As shown in FIG. 22, central hollow portion 720 may be open at inferior surface 742 of implant 700. In other embodiments, struts may be provided in central portion 752 at inferior surface 742 and central hollow portion 720 may be open at superior surface 741.

Manufacturing and Materials

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g., γTitanium Aluminides, $Ti_6$—$Al_4$—V ELI (ASTM F 136), or $Ti_6$—$Al_4$—V (ASTM F 1108 and ASTM F 1472)) and inert, biocompatible polymers, such as polyether ether ketone (PEEK) (e.g., PEEK-OPTIMA®, Invibio Inc). Optionally, the implant contains a radiopaque marker to facilitate visualization during imaging.

In different embodiments, processes for making an implant can vary. In some embodiments, the entire implant may be manufactured and assembled via injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations. In some cases, the implant may be formed by additive manufacturing (e.g., 3-D printing) in an anatomical orientation. That is, the implant may be formed from the bottom up in its regular upright position. However, in other cases, the implant may be formed by an additive manufacturing process in a non-anatomical orientation. For example, in some cases, the implant may be formed on its side. For instance, in some cases, the implant may be formed beginning with the anterior surface and concluding with the posterior surface. In some cases, the implant may be formed beginning with one lateral side and concluding with the opposing lateral side.

Provisions may be used to facilitate additive manufacturing in one or more particular orientations. For example, in some cases, additive manufacturing may be facilitated by the orientations of the struts. For example, in the orientation in which the implant is desired to be manufactured, the roof angle, i.e., the angle between the underside of a structural component and a horizontal plane, may be 30 degrees or greater. In some embodiments, the minimum roof angle may be 32 degrees.

Alternatively, or additionally, closely spaced, paper-thin vertical elements may be printed as a supportive base in order to additively manufacture structures with a roof angle of less than 30 degrees. With the vertical elements so closely spaced, there is a small enough span between the vertical elements that the horizontal structures can be added despite having a roof angle smaller than 30 degrees. Because the vertical elements are so thin, they can be easily broken away from the completed implant after the additive manufacturing process has been complete. That is, the vertical elements can be "knock-outs" or "punch-out" elements that are removed after manufacturing.

Figure 24:
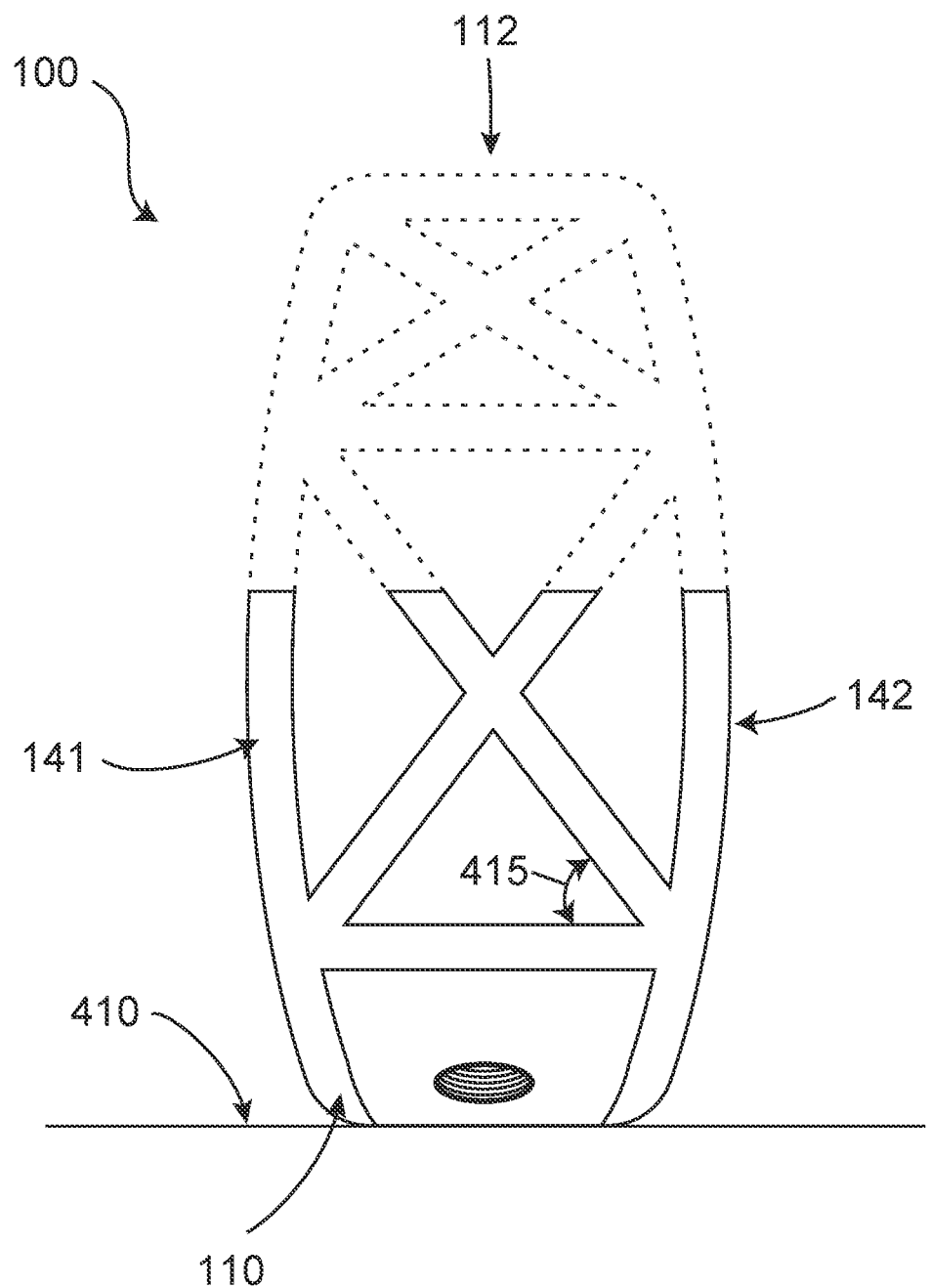
FIG. 24 is a schematic illustration of a process of manufacturing an implant with the implant partially formed.
Figure 25:
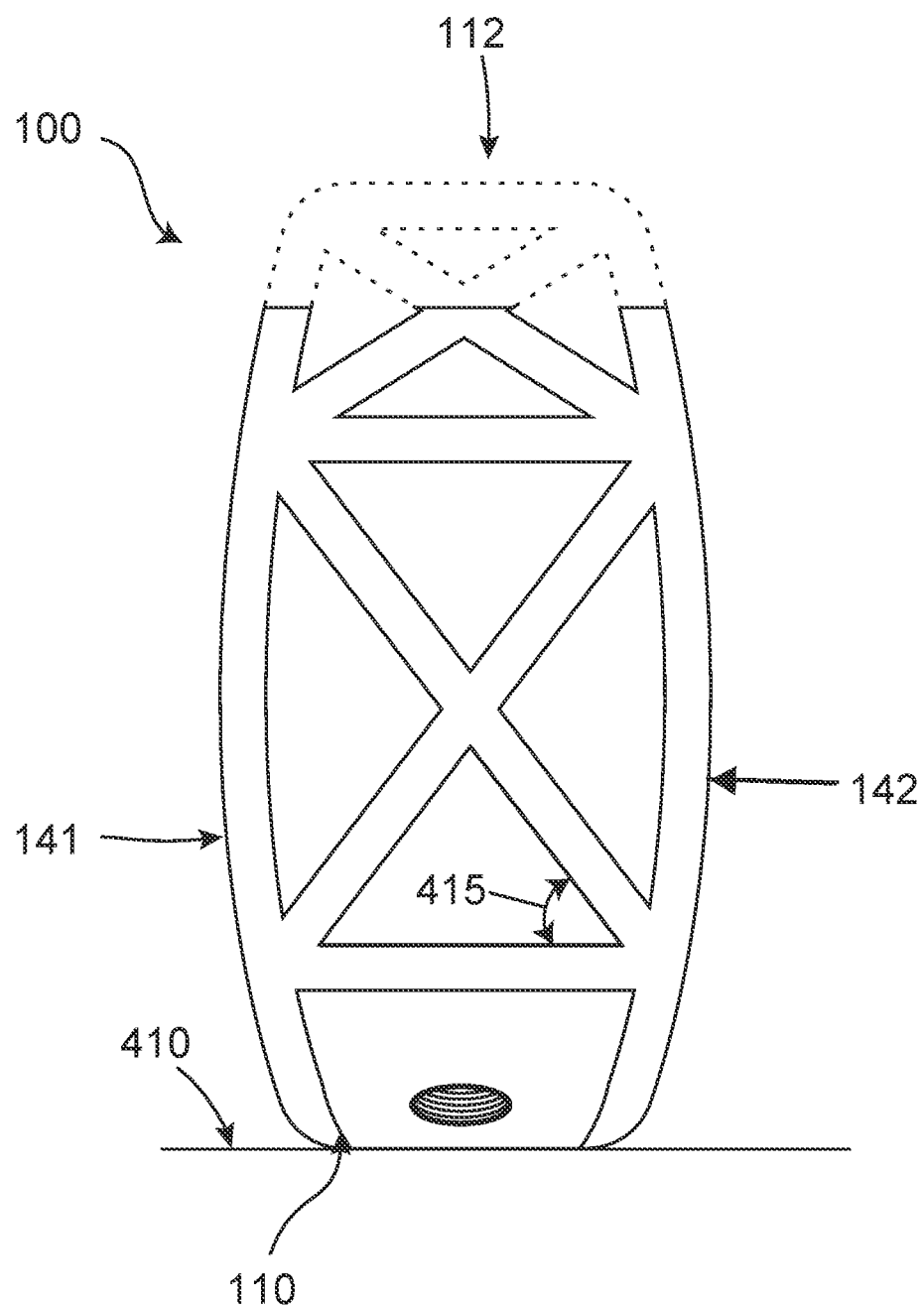
FIG. 25 is a schematic illustration of a process of manufacturing with the implant more fully formed.

Referring now to FIGS. 24 and 25, an exemplary process of manufacturing an implant according to any of the previous embodiments is illustrated. In this exemplary process, an additive manufacturing technique, for example, 3-D printing, is used to manufacture an implant. FIG. 24 illustrates implant 100 in a schematic and generic form. Accordingly, FIG. 24 should not be interpreted as illustrating the particular structural components of implant 100. Rather, FIG. 24 illustrates general concepts of implant 100, as discussed in further detail below.

According to the exemplary process, an implant, for example, implant 100, described above, is printed in a substantially vertical direction. That is, the implant is printed in a direction starting at one end along the perimeter surface of the implant (e.g., the anterior side) and continuing to add layers until forming the opposite end of the perimeter surface (e.g., the posterior side). The exemplary process described here is in contrast to printing the implant oriented in a substantially horizontal (anatomical) direction, which would be in a direction starting at the contact surface on the superior or inferior side of the implant (i.e., the top or bottom of the implant) and continuing to add layers until forming the contact surface on the opposite side of the implant.

With the exemplary process, each of the inferior and superior surfaces on opposite sides of the implant are formed in a substantially vertical direction simultaneously such that each successive layer adds material to both the inferior and superior surfaces on opposite sides of the implant during the same pass of the additive manufacturing tool.

FIG. 24 is a schematic illustration of a process of manufacturing an implant with the implant partially formed. FIG. 25 is a schematic illustration of a process of manufacturing with the implant partially, but more fully, formed. A dashed outline indicates the unformed portion of the implant in both FIGS. 24 and 25.

Referring now to FIG. 24, an implant 100 is shown in a partially printed condition during an exemplary manufacturing process. In this embodiment, the exemplary manufacturing process is an additive manufacturing process, for example, a 3-D printing process, that builds up material layer by layer to form the implant. The exemplary manufacturing process begins by additively manufacturing a first layer proximate to a base plate 410. Base plate 410 is a platform or other component that is configured to provide a surface upon which the implant may be built during the exemplary manufacturing process. As discussed above, in this exemplary process, implant 100 may be built in a substantially vertical direction. In this case, the first layer may be a portion of a perimeter surface of implant 100.

During the exemplary manufacturing process, the process involves continuing to additively manufacture the body layer by layer wherein each successive layer is disposed further from base plate 410 than the previous layer so that the body is built vertically upward, layer by layer. Accordingly, additional layers of material are built up in the vertical direction by multiple passes, with each pass adding material to the first layer and subsequent additional layers to continue to form implant 100. As shown in FIG. 24, implant 100 is in a partially manufactured condition with the anterior half formed on base plate 410 and including a plurality of struts.

During the substantially vertical manufacturing, the contact surfaces on opposite sides (superior and inferior) of implant 100 are formed in layers such that material is added to both sides during the same pass of the additive manufacturing process. For example, in FIG. 24, implant 100 includes superior surface 141 and inferior surface 142 disposed on the opposite side of implant 100. During the additive manufacturing process, each successive layer adds material to both inferior surface 142 and superior surface 141 on opposite sides of implant 100 during the same pass.

In addition, the additive manufacturing process described above can provide texture or other surface irregularities to both bone contacting surfaces (i.e., superior surface 141 and inferior surface 142) during the 3D manufacturing process. If the implant were to be formed with the inferior surface on the baseplate 410, then inferior surface 142 would have a flat, non-textured finish. However, by forming the implant starting on the anterior side and progressing in the posterior direction, texture may be formed on both the superior and inferior sides of the implant. Such texture or surface irregularities may assist with providing greater adhesion in contact with a bone of a patient.

Thus, the process may involve additively manufacturing a lower peripheral portion of the implant (i.e., an area of the peripheral portion disposed closest to the baseplate, such as the anterior part of the peripheral portion). The process may then involve additively manufacturing parts of the peripheral portion and the central portion together in the same additive layer, such that this step occurs after the step of additively manufacturing the lower peripheral portion. It will be noted that less material may be used to form the central portion than the peripheral portion so that a central truss structure is less dense than a peripheral truss structure. Subsequently, the process may involve additively manufacturing an upper peripheral portion.

As shown in FIGS. 24 and 25, each structural element of implant 100 may have roof angle 415 between the underside of the structural element and horizontal. In some embodiments, roof angle 415 may be no less than 30 degrees. In some embodiments, the minimum roof angle of all structural elements of the implant may be 30 degrees. In some cases, the minimum roof angle may be 32 degrees. This may facilitate the additive manufacturing process.

Figure 26:
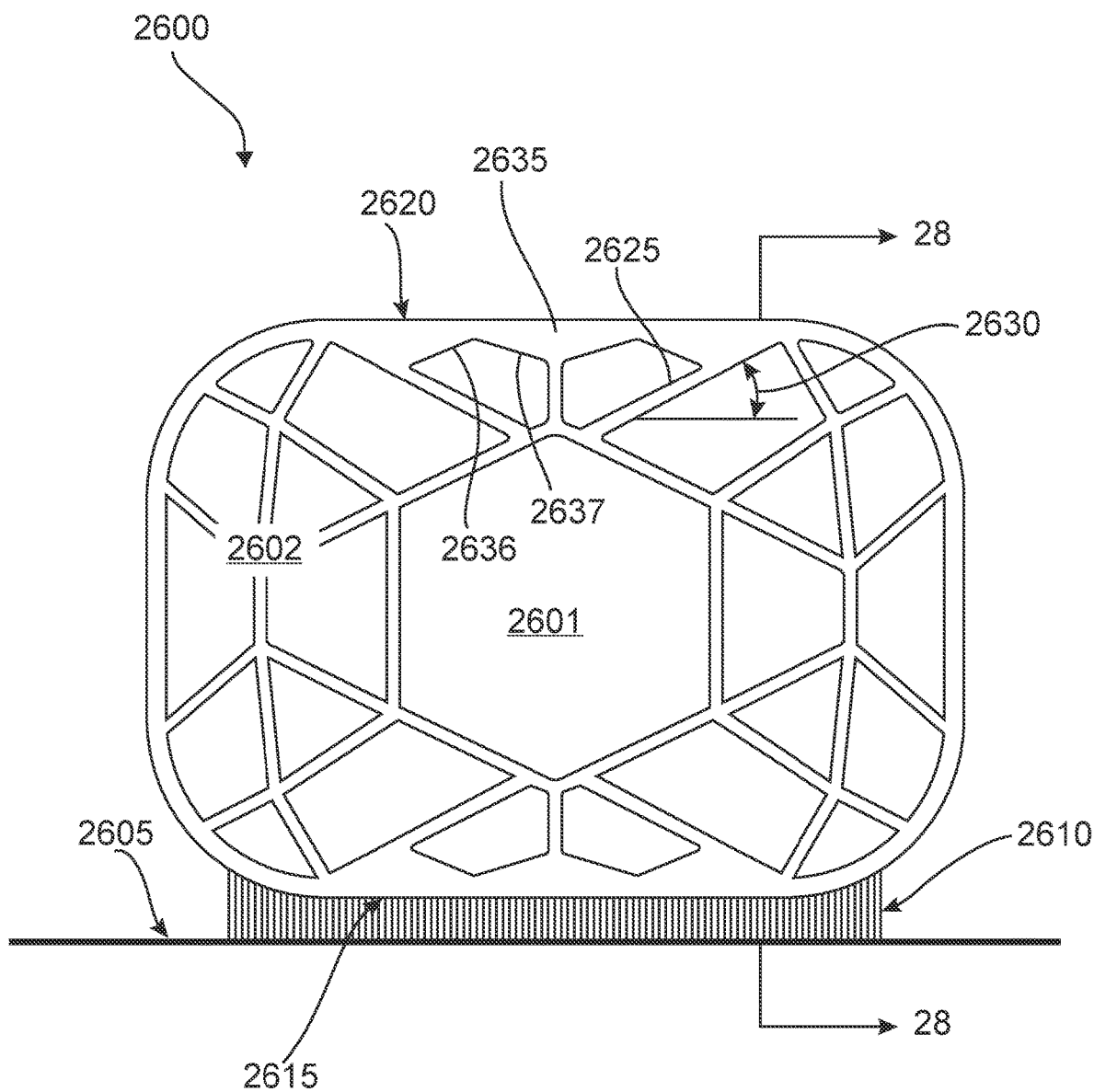
FIG. 26 is a schematic illustration of a superior view of another implant during a manufacturing process.

FIG. 26 is a schematic illustration of an implant 2600 in an additive manufacturing process. As shown in FIG. 26, implant 2600 may have a central region 2601 and an annular peripheral region 2602. Central region 2601 may be less densely populated by support structures than peripheral region 2602, as shown in FIG. 26.

As shown in FIG. 26, implant 2600 may be additively manufactured in a non-anatomical orientation, with its anterior side 2615 facing downward toward a baseplate 2605 upon which implant 2600 is additively manufactured. Implant 2600 may be formed layer by layer from anterior side 2615 to posterior side 2620 of implant 2600.

In order to facilitate the additive manufacturing of implant 2600, one or more thin vertical elements 2610 may be formed on baseplate 2605. Implant 2600 may be formed on a bed of thin vertical elements 2610. This enables the horizontally oriented surface of anterior side 2615 of implant 2600 to be formed despite having a roof angle of less than 30 degrees. Thin vertical elements 2610 are formed close enough together that the horizontally oriented surface of anterior side 2615 can be formed by additive manufacturing. By forming anterior side 2615 lifted off baseplate 2605, various surface features, such as texture, may be formed on the surface of anterior side 2615 during the additive manufacturing process.

In addition, the structural elements of implant 2600 may have a minimum roof angle of 30 degrees. For example, as illustrated in FIG. 26, a strut 2625 may have a roof angle 2630, which is 30 degrees or greater. In some embodiments, roof angle 2630 may be approximately 32 degrees. In addition, a laterally extending posterior structure 2635 may have anterior-facing surfaces that have roof angles of 30 degrees or more. For example, a first surface 2636 and a second surface 2637 of posterior structure 2635 may have roof angles of 30 degrees or more, as shown in FIG. 26. In some embodiments, all structural elements of implant 2600 may have roof angles of 30 degrees or more. For example, as shown in FIG. 26, the structural elements of implant 2600 may have a minimum roof angle of approximately 32 degrees.

Figure 27:
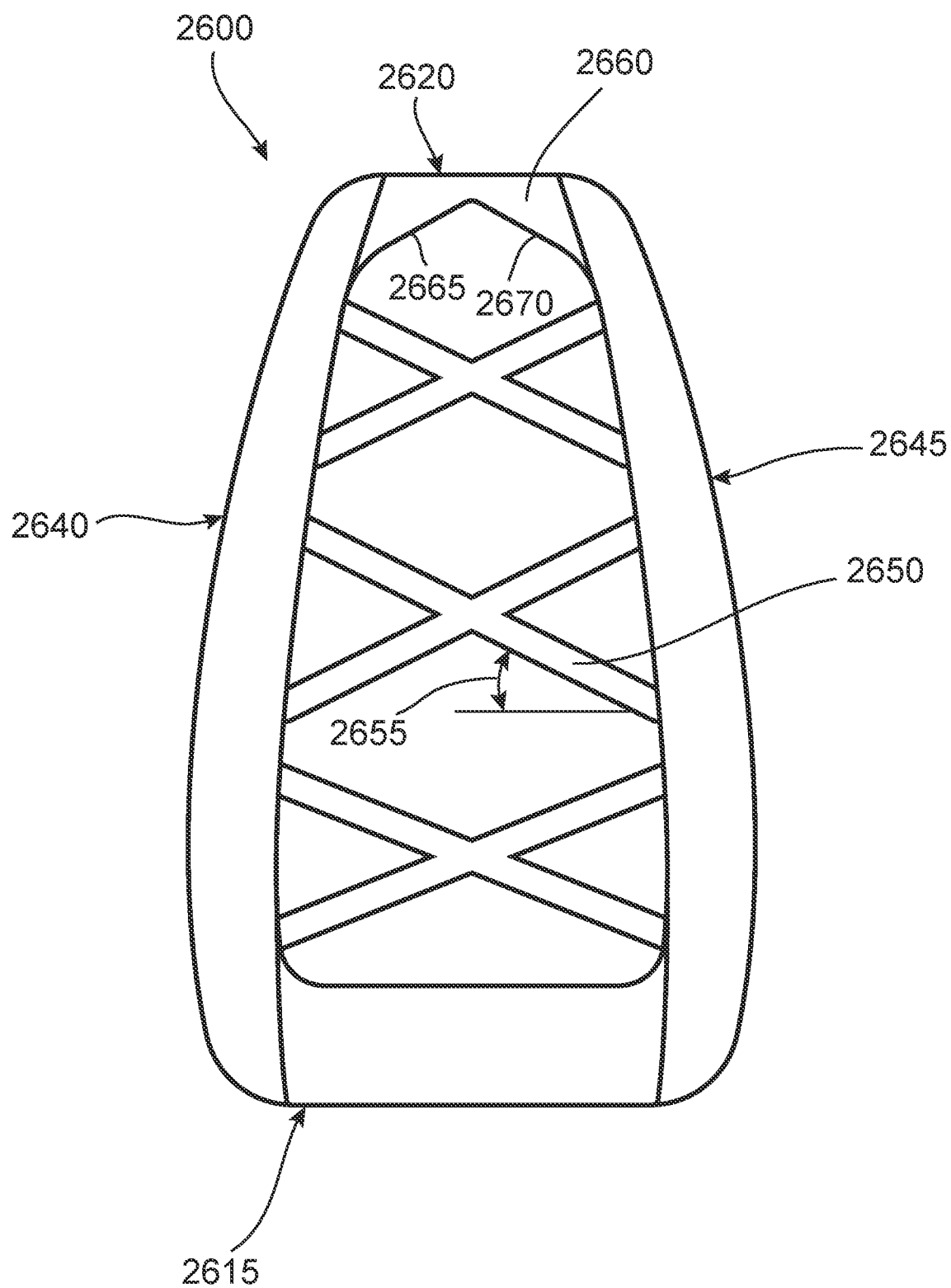
FIG. 27 is a schematic lateral view of the implant of FIG. 26.
Figure 28:
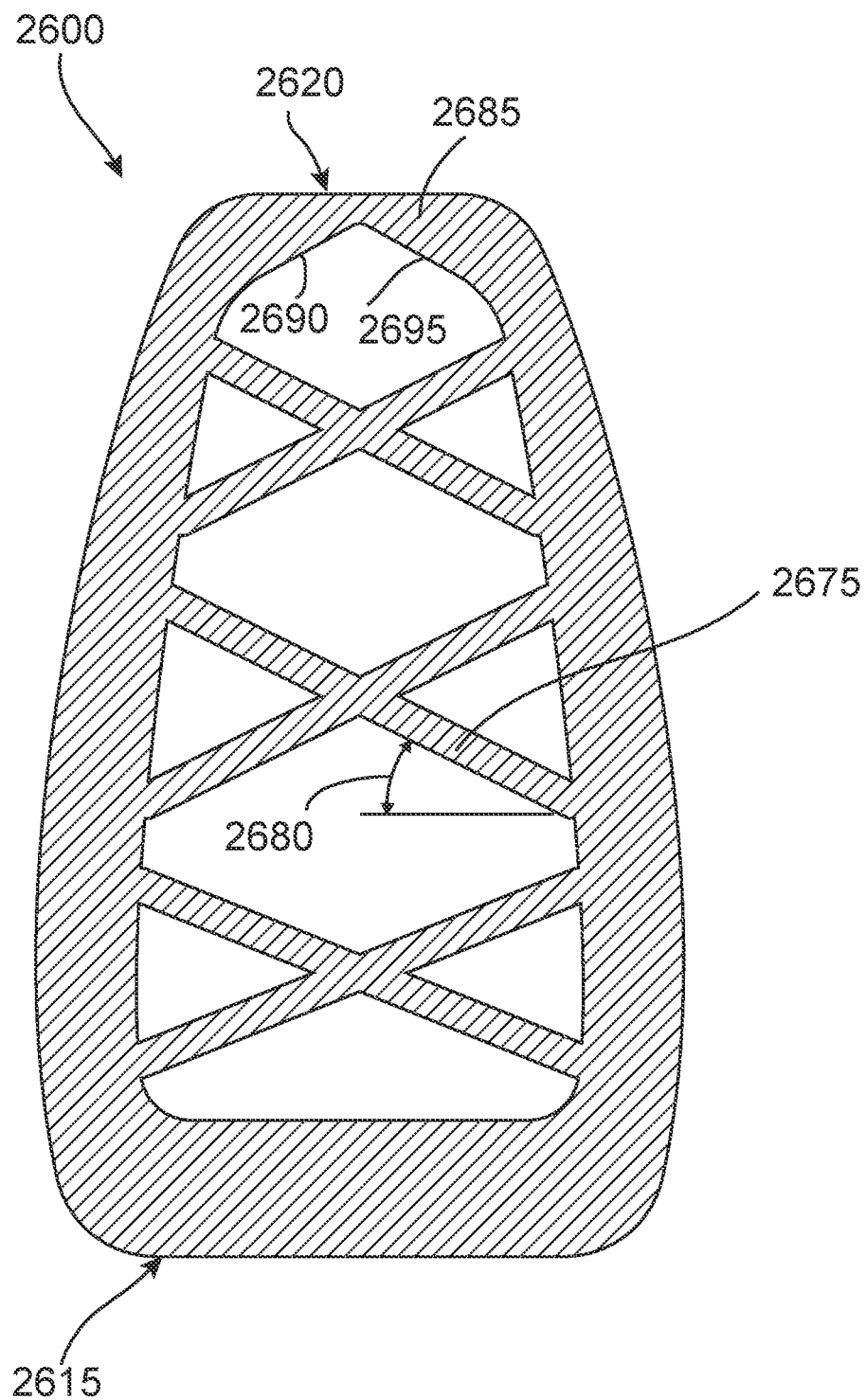
FIG. 28 is a schematic cross-sectional view of the implant of FIG. 26.

While FIG. 26 illustrates roof angles in a laterally oriented plane, it will be understood that roof angles in a vertically oriented plane may also be formed with a minimum 30-degree roof angle. FIGS. 27 and 28 illustrate the roof angles of the structures of implant 2600 in vertical planes.

FIG. 27 is a lateral view of implant 2600 when oriented standing on anterior side 2615 as it would be during the manufacturing process illustrated in FIG. 26. As shown in FIG. 27, implant 2600 also includes posterior side 2620. Further, implant 2600 may also include a superior surface 2640 and an inferior surface 2645. As shown in FIG. 27, implant 2600 may include a plurality of peripheral struts around the perimeter of implant 2600 that are arranged in X-shaped configurations. As shown in FIG. 27, first peripheral strut 2650 has a roof angle 2655. In some embodiments, roof angle 2655 may be 30 degrees or greater. For example, in some cases, roof angle 2655 may be approximately 32 degrees. In some embodiments, each of the peripheral struts may have roof angles of 30 degrees or greater. In some cases, the minimum roof angle of the peripheral struts may be approximately 32 degrees.

In addition, as also shown in FIG. 27, posterior structures extending in the superior-inferior direction, such as a posterior structure 2660, may have roof angles of 30 degrees or more. Posterior structure 2660 may have a first anterior-facing surface 2665 and a second anterior-facing surface 2670. As shown in FIG. 27, first anterior-facing surface 2665 and second anterior-facing surface 2670 may both have roof angles of 30 degrees or more. For example, in some cases, all structural elements extending in the superior-inferior direction may have a minimum roof angle of 30 degrees or more. For instance, the minimum roof angle may be approximately 32 degrees.

It will also be understood that, in addition to the peripheral structures, the internal structures of implant 2600 may also have minimum roof angles of 30 degrees or more. For example, as shown in FIG. 28, an internal strut 2675 may have a roof angle 2680. In some embodiments, roof angle 2680 may be 30 degrees or greater. For example, in some cases, roof angle 2680 may be approximately 32 degrees.

In addition, internal posterior structures, such as a posterior structure 2685, may have roof angles of 30 degrees or more. Posterior structure 2685 may have a first anterior-facing surface 2690 and a second anterior-facing surface 2695. As shown in FIG. 28, first anterior-facing surface 2690 and second anterior-facing surface 2695 may both have roof angles of 30 degrees or more. For example, in some cases, all structural elements extending in the superior-inferior direction may have a minimum roof angle of 30 degrees or more. For instance, the minimum roof angle may be approximately 32 degrees.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A method of making an intervertebral implant having a body, the body having an open truss structure, the body including opposing end surfaces, and a perimeter surface, the perimeter surface extending around an outer periphery of the body; the body also including a central portion and a peripheral portion, the peripheral portion extending from the perimeter surface inward toward the central portion; the method of making comprising the steps of:
   additively manufacturing a first layer, the first layer being proximate a base plate; the first layer forming a part of the perimeter surface;
   continuing to additively manufacture the body layer by layer wherein each successive layer is disposed further from the base plate than the previous layer so that the body is built vertically upward layer by layer, thereby producing:
   a generally annular shape with opposing end surfaces, the opposing end surfaces including a superior surface and an inferior surface,
   a first strut disposed at a boundary between the central portion and the peripheral portion and having a non-circular cross-sectional shape, the non-circular cross-sectional shape being one of oblong and an airfoil cross-sectional shape, and the non-circular cross-sectional shape having a cross-sectional length and a cross-sectional width, wherein the cross-sectional length is longer than the cross-sectional width; and wherein the first strut is oriented such that the cross-sectional length of the first strut extends in a radial direction extending from a center of the central portion to the peripheral portion in order to facilitate flow of bone graft material in the radial direction away from the central axis.

2. The method of claim 1, wherein a minimum roof angle for all structural components of the implant is 30 degrees or greater.

3. The method of claim 1, wherein the peripheral portion extends inward toward the central portion to achieve a substantially similar radial thickness around the central portion.

4. The method of claim 1, wherein the peripheral portion is sized and configured to generally correspond to a cortical bone region of a confronting vertebral body.

5. The method of claim 1, wherein the central portion is sized and configured to generally correspond to a cancellous bone region of a confronting vertebral body.

6. The method of claim 1, wherein the first strut has an airfoil cross-sectional shape.

7. The method of claim 1, wherein the body includes a second strut having a non-circular cross-sectional shape being one of oblong and an airfoil cross-sectional shape.

8. The method of claim 7, wherein the first strut and second strut cooperate to direct bone graft material into a region of the peripheral portion.

9. The method of claim 8, wherein the second strut is inclined with respect to the first strut.

10. A method of making an intervertebral implant having a body, the body having an open truss structure, the body including opposing end surfaces, and a perimeter surface, the perimeter surface extending around an outer periphery of the body; the body also including a central portion and a peripheral portion, the peripheral portion extending from the perimeter surface inward toward the central portion; the method of making comprising the steps of:

additively manufacturing a first layer, the first layer being proximate a base plate; the first layer forming a part of the perimeter surface;

continuing to additively manufacture the body layer by layer wherein each successive layer is disposed further from the base plate than the previous layer so that the body is built vertically upward layer by layer;

additively manufacturing a lower peripheral portion;

additively manufacturing the peripheral portion and the central portion in the same layer, wherein this step occurs after the step of additively manufacturing the peripheral portion, and wherein less material is used to form the central portion than the peripheral portion so that a central truss structure is less dense than a peripheral truss structure; and additively manufacturing an upper peripheral portion.

11. The method of claim 10, wherein a minimum roof angle for all structural components of the implant is 30 degrees or greater.

12. The method of claim 10, wherein the opposing end surfaces include a superior surface and an inferior surface, wherein a texture is created on the superior surface as the superior surface is additively manufactured.

13. The method of claim 12, wherein a texture is created on the inferior surface as the inferior surface is additively manufactured.

14. The method of claim 10, wherein the peripheral portion extends inward toward the central portion to achieve a substantially similar radial thickness around the central portion.

15. The method of claim 10, wherein the peripheral portion is sized and configured to generally correspond to a cortical bone region of a confronting vertebral body.

16. The method of claim 10, wherein the central portion is sized and configured to generally correspond to a cancellous bone region of a confronting vertebral body.

17. The method of claim 10, wherein the body includes a first strut disposed at a boundary between the central portion and the peripheral portion and having a non-circular cross-sectional shape, the non-circular cross-sectional shape being one of oblong and an airfoil cross-sectional shape.

18. The method of claim 17, wherein the body includes a second strut disposed at the boundary between the central portion and the peripheral portion and having a non-circular cross-sectional shape being one of oblong and an airfoil cross-sectional shape.

19. The method of claim 18, wherein the first strut and second strut cooperate to direct bone graft material into a region of the peripheral portion.

20. The method of claim 19, wherein the second strut is inclined with respect to the first strut.

* * * * *